(12) United States Patent
De Block et al.

(10) Patent No.: US 9,279,130 B2
(45) Date of Patent: Mar. 8, 2016

(54) METHODS FOR MANUFACTURING PLANT CELL WALLS COMPRISING CHITIN

(75) Inventors: Marc De Block, Merelbeke (BE); Frank Meulewaeter, Merelbeke (BE); Vincent Bulone, Täby (SE); Gea Guerriero, Naples (IT)

(73) Assignee: BAYER CROPSCIENCE NV, Belgium (BE)

( * ) Notice: Subject to any disclaimer, the term of this patent is extended or adjusted under 35 U.S.C. 154(b) by 436 days.

(21) Appl. No.: 13/522,506

(22) PCT Filed: Jan. 24, 2011

(86) PCT No.: PCT/EP2011/000365
§ 371 (c)(1),
(2), (4) Date: Nov. 9, 2012

(87) PCT Pub. No.: WO2011/089021
PCT Pub. Date: Jul. 28, 2011

(65) Prior Publication Data
US 2013/0091602 A1    Apr. 11, 2013

Related U.S. Application Data

(60) Provisional application No. 61/297,973, filed on Jan. 25, 2010.

(30) Foreign Application Priority Data

Jan. 25, 2010  (EP) .................................... 10000712

(51) Int. Cl.
| | | |
|---|---|---|
| A01H 5/00 | (2006.01) | |
| A01H 5/10 | (2006.01) | |
| C12N 15/82 | (2006.01) | |
| C12N 15/05 | (2006.01) | |
| C12N 9/10 | (2006.01) | |

(52) U.S. Cl.
CPC .......... *C12N 15/8246* (2013.01); *C12N 9/1051* (2013.01); *C12Y 204/01016* (2013.01)

(58) Field of Classification Search
None
See application file for complete search history.

(56) References Cited

U.S. PATENT DOCUMENTS

| | | | |
|---|---|---|---|
| 4,535,060 | A | 8/1985 | Comai |
| 4,769,061 | A | 9/1988 | Comai |
| 4,940,835 | A | 7/1990 | Shah et al. |
| 4,971,908 | A | 11/1990 | Kishore et al. |
| 5,004,863 | A | 4/1991 | Umbeck |
| 5,094,945 | A | 3/1992 | Comai |
| 5,145,783 | A | 9/1992 | Kishore et al. |
| 5,188,642 | A | 2/1993 | Shah et al. |
| 5,310,667 | A | 5/1994 | Eichholtz et al. |
| 5,312,910 | A | 5/1994 | Kishore et al. |
| 5,463,175 | A | 10/1995 | Barry et al. |
| 5,605,793 | A | 2/1997 | Stemmer |
| 5,627,061 | A | 5/1997 | Barry et al. |
| 5,633,435 | A | 5/1997 | Barry et al. |
| 5,792,933 | A | 8/1998 | Ma |
| 5,811,238 | A | 9/1998 | Stemmer et al. |
| 5,830,721 | A | 11/1998 | Stemmer et al. |
| 6,096,950 | A | 8/2000 | John |
| 6,166,294 | A | 12/2000 | Kasukabe et al. |
| 6,259,003 | B1 | 7/2001 | Fujisawa et al. |
| 6,483,013 | B1 | 11/2002 | Reynaerts et al. |
| 6,566,587 | B1 | 5/2003 | Lebrun et al. |
| 6,838,600 | B2 * | 1/2005 | Williams ....................... 800/314 |
| 2003/0106089 | A1 * | 6/2003 | McBride ................ C07K 14/36 800/278 |
| 2003/0106097 | A1 | 6/2003 | Haigler | |

FOREIGN PATENT DOCUMENTS

| | | | |
|---|---|---|---|
| WO | 90/12107 | 10/1990 | |
| WO | 91/02071 | 2/1991 | |
| WO | 92/15675 | 9/1992 | |
| WO | 95/06128 | 3/1995 | |
| WO | 96/38567 | 12/1996 | |
| WO | 97/04103 | 2/1997 | |
| WO | 98/30698 | 7/1998 | |
| WO | 00/09729 | 2/2000 | |
| WO | WO 00/09729 * | 2/2000 | ............. C12N 15/82 |
| WO | WO 00/09729 * | 2/2000 | ............. C12N 15/82 |
| WO | WO00/09729 * | 2/2000 | ............. C12N 15/82 |
| WO | 00/71733 A1 | 11/2000 | |
| WO | 02/10377 A1 | 2/2002 | |
| WO | 02/10413 A1 | 2/2002 | |
| WO | 03/052108 A2 | 6/2003 | |
| WO | 2005/098004 A2 | 10/2005 | |
| WO | 2006/136351 A2 | 12/2006 | |
| WO | 2009/152359 A2 | 12/2009 | |
| WO | 2010/015423 A2 | 2/2010 | |

OTHER PUBLICATIONS

Bontemps et al (Microbiology (1997), 143, 2003-2020).*
Mort-Bontemps et al (Microbiology (1997), 143, 2003-2020).*
Francesca D. Ciccarelli, et al., The identification of a conserved domain in both spartin and spastin, mutated in hereditary spastic paraplegia, Genomics, 81 (2003) 437-441.
Steven J. Clough, et al., Floral dip: a simplified method for Agrobacterium-mediated transformation of Arabidopsis thaliana, The Plant Journal (1998) 16(6), 735-743.
Keith W. Earley, et al., Gateway-compatible vectors for plant functional genomics and proteomics, The Plant Journal (2006) 45, 616-629.
Michio Inoue, et al., Nucleotide-Dependent Conformational Changes and Assembly of the AAA ATPase SKD1/VPS4B, Journal compilation 2008 Blackwell Munksgaard, doi: 10.1111/j.1600-0854.2008.00831.x.

(Continued)

*Primary Examiner* — Lee A Visone

(57) ABSTRACT

Methods and means are provided for the modification of the reactivity of plant secondary cell walls, particularly in cotton cell walls found in cotton fibers. This can be conveniently achieved by expressing a chimeric gene encoding a *Saprolegnia monoica* chitin synthase in cotton plants.

16 Claims, 2 Drawing Sheets

(56) References Cited

OTHER PUBLICATIONS

Figure 1A:

Collin Kieffer, et al., Two distinct modes of ESCRT-III recognition are required for VPS4 functions in lysosomal protein targeting and HIV-1 budding, Dev Cell. Jul. 2008; 15(1): 62-73.doi:10.1016/j.devcel.2008.05.014.

M.A. Larkin, et al., Clustal W and Clustal X version 2.0, vol. 23 No. 21 2007, pp. 2947-2948 doi: 10.1093/bioinformatics/btm404.

X.D. Liu, et al., Chitosan Coated Cotton Fiber: Preparation and Physical Properties, Carbohydrate Polymers, 44 (2001) 233-238, PII:S0144-8617 (00) 00206-X.

Leonard Machlis, Growth and Nutrition of Water Molds in the Subgenus Euallomyces. II. Optimal Composition of the Minimal Medium, 1953, Am. J. Bot: 450-460.

Maryline Mort-Bontemps, et al., CHS2, a Chitin Synthase Gene from the Oomycete Saprolegnia Monoica, Microbiology (1997) 143, 2009-2020.

Saul B. Needleman, et al., A General Method Applicable to the Search for Similarities in the Amino Acid Sequence of Two Proteins, J. Mol. Biol. (1970) 48, 443-453.

Takayuki Obita, et al., Structural Basis for Selective Recognition of ESCRT-III by the AAA ATPase Vps4, Vol Nature 449/11 735-739.

Patel et al., SPG20 is mutated in Troyer Syndrome, an hereditary Spastic Paraplegia, 2002, Nature Genetics 31: 347-348.

William R. Pearson et al., Improved Tools for Biological Sequence Comparison, 1998 Biochemistry, vol. 85, pp. 2444-2448.

Rachel Y. Samson, et al., A Role for the ESCRT System in Cell Division in Archaea, Science 322: 1710-1713.

Anna Scott, et al., Structure and ESCRT-III Protein Interactions of the MIT Domain of Human VPS4A, Proc Natl Acad Sci USA. 102: 13813-13818.

Melissa D. Stuchell-Brereton, et al., ESCRT-III Recognition by VPS4 ATPases, 2007, Nature 449: 740-744.

Suetake T. Hayashi, et al., Solution Structure of MIT Domain from human skd1., from Madej et al. MMDB: 3D structures and macromolecular interactions, Nucleic Acids Res. Jan. 2012; 40(Database issue):D461-4.

Suetake T. Hayashi, et al., Solution Structure of Mouse MIT domain, from MMadej et al. MMDB: 3D structures and macromolecular interactions, Nucleic Acids Res. Jan. 2012; 40(Database issue):D461-4.

Suetake T. Hayashi, et al., Solution Structure of MIT domain from human spartin, from Madej et al. MMDB: 3D structures and macromolecular interactions, Nucleic Acids Res. Jan. 2012; 40(Database issue):D461-4.

Hirotoshi Takasu, et al., Structural Characterization of the MIT Domain from Human Vps4b., Biochem Biophys Research Communication, 334:460-465.

Olivier Voinnet, et al., An Enhanced Transient Expression System in Plants based on Suppression of Gene Silencing by the p19 protein of Tomato Bushy Stunt Virus, The Plant Journal 33: 949-956.

Dong Yang, et al., Structural Basis for Midbody Targeting of Spastin by the ESCRT-III Protein CHMP1B, Nat Struct Biol 15: 1278-1286.

* cited by examiner

SEQUENCE LISTING

```
<160> NUMBER OF SEQ ID NOS: 24

<210> SEQ ID NO 1
<211> LENGTH: 2889
<212> TYPE: DNA
<213> ORGANISM: Saprolegnia monoica

<400> SEQUENCE: 1
atgtctgacc agctcgacct cgcggcacgc ctccgcgccc tgcgtgaggg caacgccgcg      60
ccagccgacc ccgaggcacc gccacccaca cagcctgcgc ccgcgccgca gtaccatcca     120
cagcggctgc cgccgctgta tacacaagag tcgctcgagt tcggagggac gtatgccacg     180 ggcagcccg tgggcgccga ggccgagggg tcctactcgc aagtacctgt gtggaaggac     240
tccaaggaga cgcgaagaag ttacctggac gatgagccga cgccgcagcc ccaatcgctc     300
attaacatgg ctaacacctt ggtccagcgc caagcgtcga atcaatcctt ccggcggcag     360
catacagcga acttccgacc gctgcccaac accgtcgagg agcttctgga cggcacgcca     420
acgtacgaag gagcgtttcg cctcgtgcag ctcgcggtgc agatggagca agacggcgac     480
ccaggtgctg caattaactt gtacgtggac gctggcacga cgctcgtcga agtcggtaag     540
cgtgaggtcg accctcttct gcagaagggc atccagcaaa aggcctttga gctcctgcaa     600
cgtgccgagg agctcggcac gtggatgaac acggtggccg aggaagcgcg gaaagctgcg     660
ttgccaccgc agctcaagat cgcgcgcacc aacgtcccga cggtcgagca agcgtggaag     720
ggtcgcactc cgcctttcca tgacgccgac gagttccgac ttatgcggta cacggccgtg     780
gcaacgaaag acccgatcca gttctcgaac gacggatacg tgctccgggt gcaccagcta     840
catcggcgca tcaaggtctt catcacaatc actatgtaca acgaagaagg ctcagagatc     900
ttgggcacgc tcactggtct cgccaagggc ctcgggtata tgtgcaagga gtatggccag     960 gattttggc aagaagttgc tgtggctatc gtctcagacg gccgcaccaa agctagcaag    1020
acgtgtctcg agtacctcaa cggcctcggc gcatttgacg aagagatcat gacggtcacg    1080
agcctcggtg tcgacgtgca gatgcacctc ttcgagtcga cactccagct ggttgagaac    1140
cagacgtttg aaaactactt tccgccgctc caagtgatct acgcgctcaa agagaacaac    1200
ggtggcaagc tcaactcgca tctgtggttc ttcaacgcct tcagcgagca attgaacccc    1260
aagtacactg tactcgtgga cgtcggcacc attcccgccg aaacgtccgt tttccgcttg    1320
atccgcagca tggagcgcaa ctaccagatc ggcgcgttg cggggagat tgcagtcgaa    1380 gcacctaact acttcaatcc tgtcattgcc gcacagcact tcgagtacaa gatctcaaat    1440
```

```
atcatggaca agtcgcttga gtccgtcttt ggttttatct cggtgctccc gggggccttc    1500
tcagcctacc ggtacgaagc catccgtgct gtcaagggtg tggggccgct gccagagtac    1560
tttaagagcc tcacgtcgac gaccaaagag ctcgggccat ttcagggcaa tatgtacctc    1620
gccgaagatc gtattttatg ttttgaattg ctggcgcgca acataaaca gtggacaatg     1680 cactatgtca aggacgcgat cgcccgcact gacgttcccg agacgctcgt agacctgatc    1740
aagcagcgcc ggcggtggct caacgggtct tctttgccg gcctctttgc catcgggcac     1800
tttgggcgcg tctggagcca gagctcccac accatgtccc ggaagcttgt gttcacgttt    1860
cagttctttt accttgccct acagaacctg ctcagttggt tcctcttgag caatttgttc    1920
cttacattct actttgtttt gacgctcgcc tttacggact cagcaccggc ccttctccaa    1980
gcgatgctga cgctgtatct ggccattgtc ggtggcttga ttgtctttgc gctcgggaac    2040
aagcccgaac tcggacggc cagcttttac ctcttcagct gcctttacat gggcatcatc     2100
atgatgcttg tgaccggcat ttccatctac ggccttgtcg gcaagggcac aagcgctgtg    2160
aaagacccac gggtgatcac gggggcccct ggcaactgta ctgtctctga aggggagctt    2220
gtcggtggtg tcgtcacctc gcttggcttg atcttcctct ctgccttcgt ccatggcgag    2280
tttagcatcc tcctcagcgt catccagtac ttcttcatgc tcccaacgtt tgtgaatgtg    2340
ctgggcatct atgcctacag caatttgcac gacttgagct ggggtaccaa gggcctggag    2400
tctgggggcg ccacggacc aacgaaaacc ggcggcggta acgtcaagga cgtcgtcgag      2460
cagcagaaga agctcgaagc ccaacgccag gccgcggcta aggagaaaga agatgtggac    2520
aacagcttcc gggcgttccg gtcgacactg ctgctgtcgt ggctcacgac caacggcatt    2580
tggctctacg ttgtgacgga ctacatgtcg agcgggtgct acttgaaggg cctcagcttc    2640
gtcgtcggct tctttaacgt catccgtttc acgggctgcg tcgtatttat tatccttgcgc   2700 atctttcgcc gattcggcct caactgctgt gcaatggggg ccacccacga tacctatgag    2760
cgcaacctgc cgcccgactg gcagactcat tacaatgtac agaaccaagc cgacggtcgg    2820
gttgtggtcg cccgtgcaga gagcataaac ccagcaacgc cccgcggcgg cgcctaccaa    2880
caagtctag                                                            2889
```

<210> SEQ ID NO 2
<211> LENGTH: 962
<212> TYPE: PRT
<213> ORGANISM: Saprolegnia monoica

<400> SEQUENCE: 2

```
Met Ser Asp Gln Leu Asp Leu Ala Ala Arg Leu Arg Ala Leu Arg Glu
1               5                  10                  15

Gly Asn Ala Ala Pro Ala Asp Pro Glu Ala Pro Pro Thr Gln Pro
            20                  25                  30

Ala Pro Ala Pro Gln Tyr His Pro Gln Arg Leu Pro Pro Leu Tyr Thr
        35                  40                  45

Gln Glu Ser Leu Glu Phe Gly Gly Thr Tyr Ala Thr Gly Ser Pro Val
    50                  55                  60

Gly Ala Glu Ala Glu Gly Ser Tyr Ser Gln Val Pro Val Trp Lys Asp
65                  70                  75                  80

Ser Lys Glu Thr Arg Arg Ser Tyr Leu Asp Asp Glu Pro Thr Pro Gln
                85                  90                  95

Pro Gln Ser Leu Ile Asn Met Ala Asn Thr Leu Val Gln Arg Gln Ala
            100                 105                 110
```

```
Ser Asn Gln Ser Phe Arg Arg Gln His Thr Ala Asn Phe Arg Pro Leu
        115                 120                 125

Pro Asn Thr Val Glu Glu Leu Leu Asp Gly Thr Pro Thr Tyr Glu Gly
130                 135                 140

Ala Phe Arg Leu Val Gln Leu Ala Val Gln Met Glu Gln Asp Gly Asp
145                 150                 155                 160

Pro Gly Ala Ala Ile Asn Leu Tyr Val Asp Ala Gly Thr Thr Leu Val
                165                 170                 175

Glu Val Gly Lys Arg Glu Val Asp Pro Leu Leu Gln Lys Gly Ile Gln
                180                 185                 190

Gln Lys Ala Phe Glu Leu Leu Gln Arg Ala Glu Glu Leu Gly Thr Trp
            195                 200                 205

Met Asn Thr Val Ala Glu Glu Ala Arg Lys Ala Ala Leu Pro Pro Gln
210                 215                 220

Leu Lys Ile Ala Arg Thr Asn Val Pro Thr Val Glu Gln Ala Trp Lys
225                 230                 235                 240

Gly Arg Thr Pro Pro Phe His Asp Ala Asp Glu Phe Arg Leu Met Arg
                245                 250                 255

Tyr Thr Ala Val Ala Thr Lys Asp Pro Ile Gln Phe Ser Asn Asp Gly
            260                 265                 270

Tyr Val Leu Arg Val His Gln Leu His Arg Arg Ile Lys Val Phe Ile
            275                 280                 285

Thr Ile Thr Met Tyr Asn Glu Glu Gly Ser Glu Ile Leu Gly Thr Leu
290                 295                 300

Thr Gly Leu Ala Lys Gly Leu Gly Tyr Met Cys Lys Glu Tyr Gly Gln
305                 310                 315                 320

Asp Phe Trp Gln Glu Val Ala Val Ala Ile Val Ser Asp Gly Arg Thr
                325                 330                 335

Lys Ala Ser Lys Thr Cys Leu Glu Tyr Leu Asn Gly Leu Gly Ala Phe
                340                 345                 350

Asp Glu Glu Ile Met Thr Val Thr Ser Leu Gly Val Asp Val Gln Met
            355                 360                 365

His Leu Phe Glu Ser Thr Leu Gln Leu Val Glu Asn Gln Thr Phe Glu
            370                 375                 380

Asn Tyr Phe Pro Pro Leu Gln Val Ile Tyr Ala Leu Lys Glu Asn Asn
385                 390                 395                 400

Gly Gly Lys Leu Asn Ser His Leu Trp Phe Phe Asn Ala Phe Ser Glu
                405                 410                 415

Gln Leu Asn Pro Lys Tyr Thr Val Leu Val Asp Val Gly Thr Ile Pro
            420                 425                 430

Ala Glu Thr Ser Val Phe Arg Leu Ile Arg Ser Met Glu Arg Asn Tyr
            435                 440                 445

Gln Ile Gly Gly Val Ala Gly Glu Ile Ala Val Glu Ala Pro Asn Tyr
450                 455                 460

Phe Asn Pro Val Ile Ala Ala Gln His Phe Glu Tyr Lys Ile Ser Asn
465                 470                 475                 480

Ile Met Asp Lys Ser Leu Glu Ser Val Phe Gly Phe Ile Ser Val Leu
                485                 490                 495

Pro Gly Ala Phe Ser Ala Tyr Arg Tyr Glu Ala Ile Arg Ala Val Lys
                500                 505                 510

Gly Val Gly Pro Leu Pro Glu Tyr Phe Lys Ser Leu Thr Ser Thr Thr
            515                 520                 525
```

```
Lys Glu Leu Gly Pro Phe Gln Gly Asn Met Tyr Leu Ala Glu Asp Arg
    530                 535                 540

Ile Leu Cys Phe Glu Leu Leu Ala Arg Lys His Lys Gln Trp Thr Met
545                 550                 555                 560

His Tyr Val Lys Asp Ala Ile Ala Arg Thr Asp Val Pro Glu Thr Leu
                565                 570                 575

Val Asp Leu Ile Lys Gln Arg Arg Trp Leu Asn Gly Ser Phe Phe
            580                 585                 590

Ala Gly Leu Phe Ala Ile Gly His Phe Gly Arg Val Trp Ser Gln Ser
        595                 600                 605

Ser His Thr Met Ser Arg Lys Leu Val Phe Thr Phe Gln Phe Phe Tyr
    610                 615                 620

Leu Ala Leu Gln Asn Leu Leu Ser Trp Phe Leu Ser Asn Leu Phe
625                 630                 635                 640

Leu Thr Phe Tyr Phe Val Leu Thr Leu Ala Phe Thr Asp Ser Ala Pro
                645                 650                 655

Ala Leu Leu Gln Ala Met Leu Thr Leu Tyr Leu Ala Ile Val Gly Gly
            660                 665                 670

Leu Ile Val Phe Ala Leu Gly Asn Lys Pro Glu Pro Arg Thr Ala Ser
        675                 680                 685

Phe Tyr Leu Phe Ser Cys Leu Tyr Met Gly Ile Ile Met Met Leu Val
    690                 695                 700

Thr Gly Ile Ser Ile Tyr Gly Leu Val Gly Lys Gly Thr Ser Ala Val
705                 710                 715                 720

Lys Asp Pro Arg Val Ile Thr Gly Ala Leu Gly Asn Cys Thr Val Ser
                725                 730                 735

Glu Gly Glu Leu Val Gly Gly Val Val Thr Ser Leu Gly Leu Ile Phe
            740                 745                 750

Leu Ser Ala Phe Val His Gly Glu Phe Ser Ile Leu Leu Ser Val Ile
        755                 760                 765

Gln Tyr Phe Phe Met Leu Pro Thr Phe Val Asn Val Leu Gly Ile Tyr
    770                 775                 780

Ala Tyr Ser Asn Leu His Asp Leu Ser Trp Gly Thr Lys Gly Leu Glu
785                 790                 795                 800

Ser Gly Gly Gly His Gly Pro Thr Lys Thr Gly Gly Asn Val Lys
                805                 810                 815

Asp Val Val Glu Gln Gln Lys Lys Leu Glu Ala Gln Arg Gln Ala Ala
            820                 825                 830

Ala Lys Glu Lys Glu Asp Val Asp Asn Ser Phe Arg Ala Phe Arg Ser
        835                 840                 845

Thr Leu Leu Leu Ser Trp Leu Thr Thr Asn Gly Ile Trp Leu Tyr Val
    850                 855                 860

Val Thr Asp Tyr Met Ser Ser Gly Cys Tyr Leu Lys Gly Leu Ser Phe
865                 870                 875                 880

Val Val Gly Phe Phe Asn Val Ile Arg Phe Thr Gly Cys Val Val Phe
                885                 890                 895

Ile Ile Leu Arg Ile Phe Arg Arg Phe Gly Leu Asn Cys Cys Ala Met
            900                 905                 910

Gly Ala Thr His Asp Thr Tyr Glu Arg Asn Leu Pro Pro Asp Trp Gln
        915                 920                 925

Thr His Tyr Asn Val Gln Asn Gln Ala Asp Gly Arg Val Val Val Ala
    930                 935                 940

Arg Ala Glu Ser Ile Asn Pro Ala Thr Pro Arg Gly Gly Ala Tyr Gln
```

Gln Val

<210> SEQ ID NO 3
<211> LENGTH: 2733
<212> TYPE: DNA
<213> ORGANISM: Saprolegnia monoica

<400> SEQUENCE: 3

```
atgccgccca agcgaccgac gaccgacggc cgccgcgcgt acaatgcagg caatacgact      60
gttcgcgcac ccacaaagcg cacacagccg cgcggcaaaa tcggcagccg ggcatccaat     120
aacccgagcg cggcgagcat gcaagcatac gaatttgaat acgactacaa cagcgcaatg     180
atgccaatgt tgcagccacc caagagccaa cctacgttcc tcaacaatat gcgcccatc      240
tcgtccaaag aagcgagtat gaagagctca atgcaatgc agctcttgct ccagagcact      300
tccttcacta ttgacgatgc cttccgtgcc atcgaacgcg caattcaagc tgagaacgaa     360
ggccggtacc gcgaagccct caagcatttc ttggacggtg cgagatgat tgtgactgcc      420
gccgagaagg aagcgtcgca aaaggtgcgc aacttgcttt tgcacaaagg caaggaagtg     480
ttggagtggg ccgagcacct cgccgagtgg attgagcgct ataatacgca ctccgcacca     540
gttcgcgttg ctaagcccat ggctgtcgaa gtcacgtacg accgcacgat gaattctccg     600
gatttagacg aaacggaagc gcgcacaatg ttttacacgc cagtgtgctg caccccgcaa     660
gcttttactg aaacggggta ccggctccaa tgcatccagt cgggccggcg cccgcggctt     720
atggtcgtca ttaccatgta caacgaagac gagaacgagc tccggtcgac actccgcaag     780
gtttgcaaca acgttctgta cctcaagcag cagagcctgc ctggctacga aggtgacgac     840
gcgtggaagc aggtgctcgt ggttatcgtc tcggacgggc gcaccaaagc caataaaggc     900
acgcttgagt ggcttttcgaa cgtcggcctg tatgacgaag atgtcatgaa cattacgtcg     960
acgggtgtga agtgcaatg ccatctattt gaacactcgc tgcaaatgac caaggagaac    1020
tcgatccggt ttccgccgct tcaagtgacc tttgcactaa agagcacaa cgccgggaaa     1080
cttgactcgc atctttggta tttcgacgca tttgctgaac aagtgatgcc cgactacacg    1140
gtcctcctcg atgttgggac gatgccaacc aagtcgtcct tttacaagct cctcacggcc    1200
ctcgagatca acgcgcagat tggcggtgtc tgcggcgaga tcgctgtcga taagccgctg    1260
ccaaatatgt gcaactgggt cattgccgcg cagcacttcg agtacaagat cagcaacatt    1320
ctggacaagt cactcgagtc gtgctttggc tttatatctg tgctacctgg tgcattctcc    1380
gcctatcgct acaaagcgat ccgtggtgcg ccgttgcagg cctactttaa gagtcttacg    1440
acgccgatgg cggagctcgg gccatttgct ggcaatatgt acctggctga agaccgaatc    1500
ttgtgctttg agctgctcgc gcgcaaggat tgcaactgga cgatgcacta tgtcaaggac    1560
gcgatagcac gcaccgacgt gccaacaaat ttgattgatt tggtcgggca gcgcggcgg    1620
tggctcaatg gctccttctt tgcgacactc tttgcgattt ggaactgggg tcgcgtgtac    1680
acggagagca ccactccctt cacgcgcaag atggcactgc tcgtgcagta cgtctataac    1740
gtgctccaag ttatctttc gtggttttta cccgccaact tttacctcgc tctgtatttt    1800
gtcatctttc aaggctttaa agacaatcgg tggaacttca tcgatacgtc caagtacccg    1860
gcgctgcttt tagacggcct cccgacggcg tttaacgtgt tttacgccgt caccgtgttt    1920
acccaagtca cgattggcct cgggaacaag cccaagcatg taaaaggcac gcactacctc    1980
atctcggtgc tctttggtat cctcatgctc attgcgtcca ccattgctat agtcatcttc    2040
```

-continued

```
gtcacggcgc acaagaccgt cgaagccatc atcctcgctg tcttaatcct cggcacgttc    2100
ttcattggtt cggccatgca ctgcgaagtg catcatattg tcctcacgtt tgtgcagtat    2160
acggcgctga tgccgagctt cgtcaatatc ctcatggtct actcgttctg caaccttcac    2220
gacctgagct ggggcaccaa aggcatcgac acgggtcatg agcacaagag tgacggcgcc    2280
gtcgggcagt acaaggacat cgtcgcgcgg caaaaagcgt tggaagccaa gaaggcggaa    2340
gacgccagga accaggacga gctcaagaaa cgattcgact cgttccggtc gaatttgctc    2400
ttgatttggg ttatgtccaa tatggccatg gtggtcattt gcgtcaatac aatcggcgcc    2460
gacagctacc tcccgtttct ctatgcgttt gttgccgcgt caacggcat ccggctcctc    2520 ggctgcatcg ggtacctctt gtactacgcg cgccagtttt tgctctttaa tacgctgagt    2580
gccactgggg tgctacacaa gcgccatgaa gcgcgcaagc acaagaaagc cgaagaagac    2640
ccggacccga tcgactttga atgggcact tttcagaacg accttcctga cgtcgcggtg    2700
ccgatccaag cgccgtacaa ccgcatgcgc tag                                 2733
```

<210> SEQ ID NO 4
<211> LENGTH: 910
<212> TYPE: PRT
<213> ORGANISM: Saprolegnia monoica

<400> SEQUENCE: 4

```
Met Pro Pro Lys Arg Pro Thr Thr Asp Gly Arg Ala Tyr Asn Ala
1               5                   10                  15

Gly Asn Thr Thr Val Arg Ala Pro Thr Lys Arg Thr Gln Pro Arg Gly
            20                  25                  30

Lys Ile Gly Ser Arg Ala Ser Asn Asn Pro Ser Ala Ala Ser Met Gln
        35                  40                  45

Ala Tyr Glu Phe Glu Tyr Asp Tyr Asn Ser Ala Met Met Pro Met Leu
    50                  55                  60

Gln Pro Pro Lys Ser Gln Pro Thr Phe Leu Asn Asn Ile Ala Pro Ile
65                  70                  75                  80

Ser Ser Lys Glu Ala Ser Met Lys Ser Ser Asn Ala Met Gln Leu Leu
                85                  90                  95

Leu Gln Ser Thr Ser Phe Thr Ile Asp Asp Ala Phe Arg Ala Ile Glu
            100                 105                 110

Arg Ala Ile Gln Ala Glu Asn Glu Gly Arg Tyr Arg Glu Ala Leu Lys
        115                 120                 125

His Phe Leu Asp Gly Gly Glu Met Ile Val Thr Ala Ala Glu Lys Glu
    130                 135                 140

Ala Ser Gln Lys Val Arg Asn Leu Leu Leu His Lys Gly Lys Glu Val
145                 150                 155                 160

Leu Glu Trp Ala Glu His Leu Ala Glu Trp Ile Glu Arg Tyr Asn Thr
                165                 170                 175

His Ser Ala Pro Val Arg Val Ala Lys Pro Met Ala Val Glu Val Thr
            180                 185                 190

Tyr Asp Arg Thr Met Asn Ser Pro Asp Leu Asp Glu Thr Glu Ala Arg
        195                 200                 205

Thr Met Phe Tyr Thr Pro Val Cys Cys Thr Pro Gln Ala Phe Thr Glu
    210                 215                 220

Thr Gly Tyr Arg Leu Gln Cys Ile Gln Ser Gly Arg Arg Pro Arg Leu
225                 230                 235                 240

Met Val Val Ile Thr Met Tyr Asn Glu Asp Glu Asn Glu Leu Arg Ser
```

```
                     245                 250                 255
Thr Leu Arg Lys Val Cys Asn Asn Val Leu Tyr Leu Lys Gln Gln Ser
            260                 265                 270

Leu Pro Gly Tyr Glu Gly Asp Ala Trp Lys Gln Val Leu Val Val
        275                 280                 285

Ile Val Ser Asp Gly Arg Thr Lys Ala Asn Lys Gly Thr Leu Glu Trp
    290                 295                 300

Leu Ser Asn Val Gly Leu Tyr Asp Glu Asp Val Met Asn Ile Thr Ser
305                 310                 315                 320

Thr Gly Val Lys Val Gln Cys His Leu Phe Glu His Ser Leu Gln Met
                325                 330                 335

Thr Lys Glu Asn Ser Ile Arg Phe Pro Pro Leu Gln Val Thr Phe Ala
            340                 345                 350

Leu Lys Glu His Asn Ala Gly Lys Leu Asp Ser His Leu Trp Tyr Phe
        355                 360                 365

Asp Ala Phe Ala Glu Gln Val Met Pro Asp Tyr Thr Val Leu Leu Asp
    370                 375                 380

Val Gly Thr Met Pro Thr Lys Ser Ser Phe Tyr Lys Leu Leu Thr Ala
385                 390                 395                 400

Leu Glu Ile Asn Ala Gln Ile Gly Gly Val Cys Gly Glu Ile Ala Val
                405                 410                 415

Asp Lys Pro Leu Pro Asn Met Cys Asn Trp Val Ile Ala Ala Gln His
            420                 425                 430

Phe Glu Tyr Lys Ile Ser Asn Ile Leu Asp Lys Ser Leu Glu Ser Cys
        435                 440                 445

Phe Gly Phe Ile Ser Val Leu Pro Gly Ala Phe Ser Ala Tyr Arg Tyr
    450                 455                 460

Lys Ala Ile Arg Gly Ala Pro Leu Gln Ala Tyr Phe Lys Ser Leu Thr
465                 470                 475                 480

Thr Pro Met Ala Glu Leu Gly Pro Phe Ala Gly Asn Met Tyr Leu Ala
                485                 490                 495

Glu Asp Arg Ile Leu Cys Phe Glu Leu Leu Ala Arg Lys Asp Cys Asn
            500                 505                 510

Trp Thr Met His Tyr Val Lys Asp Ala Ile Ala Arg Thr Asp Val Pro
        515                 520                 525

Thr Asn Leu Ile Asp Leu Val Gly Gln Arg Arg Arg Trp Leu Asn Gly
    530                 535                 540

Ser Phe Phe Ala Thr Leu Phe Ala Ile Trp Asn Trp Gly Arg Val Tyr
545                 550                 555                 560

Thr Glu Ser Asn His Ser Phe Thr Arg Lys Met Ala Leu Leu Val Gln
                565                 570                 575

Tyr Val Tyr Asn Val Leu Gln Val Ile Phe Ser Trp Phe Leu Pro Ala
            580                 585                 590

Asn Phe Tyr Leu Ala Leu Tyr Phe Val Ile Phe Gln Gly Phe Lys Asp
        595                 600                 605

Asn Arg Trp Asn Phe Ile Asp Thr Ser Lys Tyr Pro Ala Leu Leu Leu
    610                 615                 620

Asp Gly Leu Pro Thr Ala Phe Asn Val Phe Tyr Ala Val Thr Val Phe
625                 630                 635                 640

Thr Gln Val Thr Ile Gly Leu Gly Asn Lys Pro Lys His Val Lys Gly
                645                 650                 655

Thr His Tyr Leu Ile Ser Val Leu Phe Gly Ile Leu Met Leu Ile Ala
            660                 665                 670
```

```
Ser Thr Ile Ala Ile Val Ile Phe Val Thr Ala His Lys Thr Val Glu
        675                 680                 685

Ala Ile Ile Leu Ala Val Leu Ile Leu Gly Thr Phe Phe Ile Gly Ser
690                 695                 700

Ala Met His Cys Glu Val His Ile Val Leu Thr Phe Val Gln Tyr
705                 710                 715                 720

Thr Ala Leu Met Pro Ser Phe Val Asn Ile Leu Met Val Tyr Ser Phe
                725                 730                 735

Cys Asn Leu His Asp Leu Ser Trp Gly Thr Lys Gly Ile Asp Thr Gly
            740                 745                 750

His Glu His Lys Ser Asp Gly Ala Val Gly Gln Tyr Lys Asp Ile Val
        755                 760                 765

Ala Arg Gln Lys Ala Leu Glu Ala Lys Lys Ala Glu Asp Ala Arg Asn
770                 775                 780

Gln Asp Glu Leu Lys Lys Arg Phe Asp Ser Phe Arg Ser Asn Leu Leu
785                 790                 795                 800

Leu Ile Trp Val Met Ser Asn Met Ala Met Val Ile Cys Val Asn
                805                 810                 815

Thr Ile Gly Ala Asp Ser Tyr Leu Pro Phe Leu Tyr Ala Phe Val Ala
        820                 825                 830

Ala Phe Asn Gly Ile Arg Leu Leu Gly Cys Ile Gly Tyr Leu Leu Tyr
        835                 840                 845

Tyr Ala Arg Gln Phe Leu Leu Phe Asn Thr Leu Ser Ala Thr Gly Val
850                 855                 860

Leu His Lys Arg His Glu Ala Arg Lys His Lys Ala Glu Glu Asp
865                 870                 875                 880

Pro Asp Pro Ile Asp Phe Glu Met Gly Thr Phe Gln Asn Asp Leu Pro
                885                 890                 895

Asp Val Ala Val Pro Ile Gln Ala Pro Tyr Asn Arg Met Arg
            900                 905                 910

<210> SEQ ID NO 5
<211> LENGTH: 30
<212> TYPE: DNA
<213> ORGANISM: Artificial Sequence
<220> FEATURE:
<223> OTHER INFORMATION: Primer CHS2Fwd

<400> SEQUENCE: 5
caccatgagt gaccagctcg acctcgcggc                                    30

<210> SEQ ID NO 6
<211> LENGTH: 30
<212> TYPE: DNA
<213> ORGANISM: Artificial Sequence
<220> FEATURE:
<223> OTHER INFORMATION: Primer CHS2Rev

<400> SEQUENCE: 6
tgctctctgc acgggcaacc acaacccgac                                    30

<210> SEQ ID NO 7
<211> LENGTH: 27
<212> TYPE: DNA
<213> ORGANISM: Artificial Sequence
<220> FEATURE:
<223> OTHER INFORMATION: Primer CHS1Fwd

<400> SEQUENCE: 7
```
aatgaggacg agaacgagct ccggtcg                                       27

<210> SEQ ID NO 8
<211> LENGTH: 27
<212> TYPE: DNA
<213> ORGANISM: Artificial Sequence
<220> FEATURE:
<223> OTHER INFORMATION: Primer CHS1Rev

<400> SEQUENCE: 8
agcttgtaaa aggacgactt ggttggc                                       27

<210> SEQ ID NO 9
<211> LENGTH: 28
<212> TYPE: DNA
<213> ORGANISM: Artificial Sequence
<220> FEATURE:
<223> OTHER INFORMATION: Primer CHS1Rev1

<400> SEQUENCE: 9
tctccttggt catttgcagc gagtgttc                                      28

<210> SEQ ID NO 10
<211> LENGTH: 28
<212> TYPE: DNA
<213> ORGANISM: Artificial Sequence
<220> FEATURE:
<223> OTHER INFORMATION: Primer CHS1Rev2

<400> SEQUENCE: 10
cagaacgttg ttgcaaacct tgcggagt                                      28

<210> SEQ ID NO 11
<211> LENGTH: 28
<212> TYPE: DNA
<213> ORGANISM: Artificial Sequence
<220> FEATURE:
<223> OTHER INFORMATION: Primer CHSFwd1

<400> SEQUENCE: 11
tccggtcgac actccgcaag gtttgcaa                                      28

<210> SEQ ID NO 12
<211> LENGTH: 28
<212> TYPE: DNA
<213> ORGANISM: Artificial Sequence
<220> FEATURE:
<223> OTHER INFORMATION: Primer CHS1Fwd2

<400> SEQUENCE: 12
actacacggt cctcctcgat gttgggac                                      28

<210> SEQ ID NO 13
<211> LENGTH: 24
<212> TYPE: DNA
<213> ORGANISM: Artificial Sequence
<220> FEATURE:
<223> OTHER INFORMATION: Primer CHS2Fwd1

<400> SEQUENCE: 13
tgtcggtggc ttgattgtct ttgc                                          24

<210> SEQ ID NO 14
<211> LENGTH: 24
<212> TYPE: DNA

-continued

```
<213> ORGANISM: Artificial Sequence
<220> FEATURE:
<223> OTHER INFORMATION: Primer CHS2Fwd2

<400> SEQUENCE: 14
tttggctcta cgttgtgacg gact                                          24

<210> SEQ ID NO 15
<211> LENGTH: 30
<212> TYPE: DNA
<213> ORGANISM: Artificial Sequence
<220> FEATURE:
<223> OTHER INFORMATION: Primer CHS1FLFwd

<400> SEQUENCE: 15
caccatgccg cccaagcgac cgacgaccga                                    30

<210> SEQ ID NO 16
<211> LENGTH: 28
<212> TYPE: DNA
<213> ORGANISM: Artificial Sequence
<220> FEATURE:
<223> OTHER INFORMATION: Primer CHS1FLRev

<400> SEQUENCE: 16
ctagcgcatg cggttgtacg gcgcttgg                                      28

<210> SEQ ID NO 17
<211> LENGTH: 28
<212> TYPE: DNA
<213> ORGANISM: Artificial Sequence
<220> FEATURE:
<223> OTHER INFORMATION: CHS2FLRev

<400> SEQUENCE: 17
ttagacttgt tggtaggcgc cgccgcgg                                      28

<210> SEQ ID NO 18
<211> LENGTH: 2889
<212> TYPE: DNA
<213> ORGANISM: Artificial Sequence
<220> FEATURE:
<223> OTHER INFORMATION: modified nucleotide sequence of Saprolegnia
      monoica chitin synthase 2 (codon optimized for expression in
      cotton)

<400> SEQUENCE: 18
atgagtgatc aacttgacct cgcagcaagg ttacgagcat taagagaggg taatgcagct     60
cctgctgatc ctgaagcacc tccacctaca caacctgctc cagcacccca ataccatcca    120
cagagattac cacccctcta tacacaagag agtctggagt ttggtgggac ttatgctact    180
ggatctcctg tcggagctga agctgaagga tcctatagtc aagtcccggt gtggaaggat    240
tctaaagaaa ctcgtcgctc ttacttggat gatgagccaa ctccgcaacc acagtcactc    300
attaacatgg caaacacctt ggtccagcgt caagcctcta atcaatcctt caggcgtcag    360
catactgcta atttccgacc tctgccaaac actgtcgaag agcttttgga cggaacacca    420
acctacgaag gtgcttttcg attggttcaa cttgctgtgc agatggagca agatggcgac    480
ccaggtgcag caattaacct ttacgtcgat gctggtacaa ctctcgttga agtcggtaaa    540
cgtgaggtag accctctact tcagaagggt atccagcaga aggcctttga acttctgcaa    600
cgtgctgaag agttggggac ttggatgaat actgttgccg aagaagcaag gaaagctgct    660
ttgccacctc aactcaagat tgctagaaca aacgtcccga ctgtcgaaca agcatggaaa    720
```

```
ggaagaactc ctcctttcca tgacgctgac gagtttcgct tgatgaggta tactgctgtg    780
gctaccaaag atccgatcca gttctctaac gacggatacg tgcttcgagt tcaccaacta    840
catcggagga tcaaggtctt catcacaatc actatgtaca acgaagaagg gtccgagatc    900
ttgggaactc ttactggact tgctaaggga ctcggctata tgtgcaagga gtatggccaa    960 gattttggc aagaggtcgc tgttgctatc gtgtcagatg ggagaaccaa agctagtaag    1020
acatgtctgg agtacttgaa cggcctcggt gcttttgacg aagagataat gaccgttact    1080
tcgcttggtg tcgacgtgca gatgcacttg tttgagagca cactccaact ggttgagaac    1140
cagacattcg aaaactactt tccgcccttg caagtgatct acgctctgaa ggagaacaat    1200
ggagggaaac tgaatagcca tctctggttc ttcaacgcct tttcggagca attgaatccc    1260
aagtatactg tgctcgtgga cgttggaaca attcccgctg aaacctccgt ttttcggttg    1320
atccgaagca tggaaaggaa ctaccagatt ggaggggttg ctggagagat agcagtcgaa    1380
gctcccaact acttcaatcc tgtgattgcc gctcagcact tcgagtacaa gatcagcaat    1440
atcatggaca agagccttga aagcgtgttc gggtttatat ccgttcttcc tggggctttt    1500
tcggcttatc gttacgaagc catacgtgct gtcaagggtg tcggaccttt gccagagtac    1560
ttcaagagcc tcacttcaac caccaaagaa ctcggtccat tccaggggaa tatgtatctc    1620
gccgaagatc ggattctctg tttcgaactg ctcgcaagga acataaaca gtggaccatg    1680 cactatgtga aggacgcaat cgctagaact gatgttcctg agacactcgt cgatctgatc    1740
aagcaacgac gtaggtggtt gaacggatct ttctttgccg gactctttgc aatcggacac    1800
tttggaaggg tatggtccca gtcttcacac acaatgtcca gaaagctcgt cttcaccttc    1860
cagttcttct accttgccct tcagaatctc ctcagttggt tcctcttgag caatctgttc    1920
ctgaccttct acttcgtcct tactctcgcc tttaccgatt cagctcctgc tctactccaa    1980
gctatgctta ccctgtatct ggccattgtt ggtggcttga ttgtctttgc ctcggcaac    2040 aagcccgaac ctagaacagc ctcattctac ctgttcagct gcctttacat ggggatcata    2100
atgatgctcg tgactggcat ttcgatctac ggtcttgttg gcaaaggtac aagcgctgtg    2160
aaagatccaa gggtgataac tggagcccct gggaattgta ctgtctctga aggtgaactt    2220
gtgggaggtg tcgttacttc acttggcttg atcttcctgt cagcattcgt tcatggcgag    2280
ttctccatcc tcctttcagt gatccagtac ttcttcatgc ttccgacctt tgtcaatgtg    2340
ctcgggatct atgcctattc caatctgcac gatttgagct ggggtaccaa gggactcgaa    2400
tctgggggtg gacatggtcc aacaaaaact ggtggggaa atgtgaaaga cgtcgtcgag    2460
cagcaaaaga aactcgaagc tcaaagacaa gccgcagcta aggagaaaga ggatgtggac    2520
aattcgtttc gcgcttttccg atctactctg ttgctgagtt ggctcactac caatgggatt    2580
tggctctacg ttgtgacaga ctacatgtca tctgggtgct acttgaaggg actcagtttc    2640
gttgtcggct tcttcaacgt catccagatt actggctgcg tcgtctttat aatccttcga    2700
atctttaggc ggtttggctt gaactgctgt gcaatgggtg caacacacga tacctatgag    2760
cgtaacctac ctcccgattg gcaaacccat tacaatgtcc agaaccaagc tgacggtcgg    2820
gtggtagtcg caagagccga gagtataaac ccagcaactc aagaggagg tgcttaccaa    2880 caagtctaa                                                             2889
```

<210> SEQ ID NO 19
<211> LENGTH: 69
<212> TYPE: PRT

<213> ORGANISM: Artificial Sequence
<220> FEATURE:
<223> OTHER INFORMATION: MIT domain from Saprolegnia monoica chitin synthase 2 gene

<400> SEQUENCE: 19

```
Thr Tyr Glu Gly Ala Phe Arg Leu Val Gln Leu Ala Val Gln Met Glu
1               5                   10                  15

Gln Asp Gly Asp Pro Gly Ala Ala Ile Asn Leu Tyr Val Asp Ala Gly
            20                  25                  30

Thr Thr Leu Val Glu Val Gly Lys Arg Glu Val Asp Pro Leu Leu Gln
        35                  40                  45

Lys Gly Ile Gln Gln Lys Ala Phe Glu Leu Leu Gln Arg Ala Glu Glu
    50                  55                  60

Leu Gly Thr Trp Met
65
```

<210> SEQ ID NO 20
<211> LENGTH: 69
<212> TYPE: PRT
<213> ORGANISM: Artificial Sequence
<220> FEATURE:
<223> OTHER INFORMATION: MIT domain from Saprolegnia monoica chitin synthase 1 gene

<400> SEQUENCE: 20

```
Thr Ile Asp Asp Ala Phe Arg Ala Ile Glu Arg Ala Ile Gln Ala Glu
1               5                   10                  15

Asn Glu Gly Arg Tyr Arg Glu Ala Leu Lys His Phe Leu Asp Gly Gly
            20                  25                  30

Glu Met Ile Val Thr Ala Ala Glu Lys Glu Ala Ser Gln Lys Val Arg
        35                  40                  45

Asn Leu Leu Leu His Lys Gly Lys Glu Val Leu Glu Trp Ala Glu His
    50                  55                  60

Leu Ala Glu Trp Ile
65
```

<210> SEQ ID NO 21
<211> LENGTH: 2676
<212> TYPE: DNA
<213> ORGANISM: Saprolegnia parasitica

<400> SEQUENCE: 21

```
atgccaccca agcgcccgac cgaggccagt ggccgccgct acgcgccgcc cgccggtcgt      60
ccgtccaaca acgccgccaa tgccaagccg cgcgcgccgc gaaagggcgt gagcagccgt     120
gcgtccaacg tccatccgc cgcctcgtcg tacgagtacg actacgagta caacatgatg     180
ccgatgatgc aggcgccgcc caagtcgcag ccaaccttcc tctccaacat tgcgcccatc     240
tcggcgaaag aggcgagcat gaagggctcg aacgcgatgc aactcctgct gcagggcacg     300
tcgttcacga tcgacgatgc gttccgcgcg atcgagcgtg cgatccaagc cgagaacgag     360
ggccggttcc gcgaggcgct caagcacttt ctggacggcg gcgagatgat tgtgacggcc     420
gccgagaagg aagcgtccca gaaggtccgc aacctcctcc tccataaagg caaggaggtg     480
ctcgagtggg ccgagcacct cgccgagtgg atcgagcgct acaacacgtc gacgccgccg     540
gtccgcatcg ccaagccgat ggccgtcgag gtcacgtacg accgcacgat gaactcgcca     600
gacctcgacg aaaccgaggc gcgcatgatg ttttacacgc ccgtgtgctc gggccccgaaa    660 gcgttcaccg agacggggta ccggctgcag tgcatccaga gcggccgccg cccgcggctc     720
```

```
atggtggtca tcaccatgta caacgaagac gagaacgagc tccggtcgac gctccgcaag    780
gtctgcaaca acgtcctgta cctcaagcag cacagcctcc cggggtacga aggcgacgac    840
gcgtggaagc aggtgctggt cgtcgtcgtc tcggatggcc gcacgaaagc caacaaaggc    900
acgctcgagt ggctcgccaa cgtcggcctc tacgacgaag acgttatgaa catcacgtcg    960
accggcgtca aggtgcagtg ccacctcttc gagcattcgc ttcagatgac gaaagagaac   1020
tcgatccggt tcccgccact ccaactcgac tcgcacctct ggtactttga cgcgtttgcc   1080
gagcagatca tgcccgacta caccgtgctc ctcgacgtcg gcacgatgcc gaccaagtcg   1140
tcgttctaca agctgctcac ggcgctcgag atcaacgcac agatcggcgg cgtctgcggc   1200
gagattgcgg tcgacaagcc gctgcccaac atgtgcaact gggtcatcgc ggcgcagcat   1260
ttcgaataca gatttccaa catcctcgac aagtcgctcg agtcgtgctt cggcttcatc    1320
tcggtgctgc ccggcgcgtt ctcggcctac cgctacaagg cgattcgcgg cgcgccactg   1380
caagcgtact ttaagagtct cacaaccgac atggccgagc tcggaccgtt tgctggcaac   1440
atgtacctcg ccgaagatcg catcctgtgc tttgagctcc tcgcgcgcaa agactgcaac   1500
tggaccatgc actacgtcaa ggacgcgatc gcgcgcacag acgtgccgac caacttgatc   1560
gacctcgtgg ccagcgccg cgctggctc aacgggtcgt ttttcgcgac gttgtttgcg    1620
atctggaact ggggccgcgt gtacaccgag tcgaaccact cgctcacgcg caagctcgcg   1680
ctcctcgtgc atgctcttct cggcgtctca gcggccaact tttacctcgc cttgtacttt   1740
gtcatcttcc aaggcttccg cgacaaccgg tggaacttca tcgacacgtc cgagtacccg   1800
cagtgggtcc tcgacggcct cccgacggcg tttaacgtct tttacgcggt cacggtcttt   1860
acccaagtca cgatcggcct cggcaacaag cccaaacacg tcaaaggcac ccattacctc   1920
atctcggtgc tctttggctt gctcatgctg ctcgcatccg gtgtcgccat cgtcatcttc   1980
atcacgtcct cgaaagacgc catggcgatc gtgctcgcag tgctcattct cggcacgttc   2040
ttcattgggt cagcgctgca ctgcgaagtg caccacattg tgctcacgtt cgtccagtac   2100
acggcgctca tgccgagctt tgtcaacatc ctcatggtct actcgttctg caacctccac   2160
gacctcagct ggggcacaaa gggcatcgac acgggccacg aggcccataa aaccgaagcc   2220
gtcggccagt acaaggacat tgtcgcgcgc caaaaagctc tggaggccaa gaaagcccaa   2280
gacgcgcgca accaagacga gctcaagaag cgcttcgact cgttccggtc caacttgcta   2340
ctggtgtggg tcatgtccaa catgtcgatg tcatcatct gcgtcaacac ggtcggcgcc    2400
gactcgttct tgccgttctt gtacgcgttc gtcgccgcct tcaacggcat ccggctcctc   2460
ggctgcatcg ggtacctcat ctactacgcg cggcagttcc tcctcttcaa tacgctgagc   2520
gccacgggcg tcctccacaa cgccacgaa gcgcgcaagc acaagaaggc cgaggacccg    2580
gacccgatcg acatggaact cggcacgttc aacgaaccgg cgacgtccga gattggcgcg   2640
cccatgatgc aagcgccgta caaccgcatg cgttag                             2676
```

<210> SEQ ID NO 22
<211> LENGTH: 891
<212> TYPE: PRT
<213> ORGANISM: Saprolegnia parasitica

<400> SEQUENCE: 22

Met Pro Pro Lys Arg Pro Thr Glu Ala Ser Gly Arg Arg Tyr Ala Pro
1               5                   10                  15

Pro Ala Gly Arg Pro Ser Asn Asn Ala Ala Asn Ala Lys Pro Arg Ala

```
                20              25              30
Pro Arg Lys Gly Val Ser Ser Arg Ala Ser Asn Val Pro Ser Ala Ala
            35              40              45
Ser Ser Tyr Glu Tyr Asp Tyr Glu Tyr Asn Met Met Pro Met Met Gln
50              55              60
Ala Pro Pro Lys Ser Gln Pro Thr Phe Leu Ser Asn Ile Ala Pro Ile
65              70              75              80
Ser Ala Lys Glu Ala Ser Met Lys Gly Ser Asn Ala Met Gln Leu Leu
            85              90              95
Leu Gln Gly Thr Ser Phe Thr Ile Asp Asp Ala Phe Arg Ala Ile Glu
            100             105             110
Arg Ala Ile Gln Ala Glu Asn Glu Gly Arg Phe Arg Glu Ala Leu Lys
            115             120             125
His Phe Leu Asp Gly Gly Glu Met Ile Val Thr Ala Ala Glu Lys Glu
            130             135             140
Ala Ser Gln Lys Val Arg Asn Leu Leu Leu His Lys Gly Lys Glu Val
145             150             155             160
Leu Glu Trp Ala Glu His Leu Ala Glu Trp Ile Glu Arg Tyr Asn Thr
            165             170             175
Ser Thr Pro Pro Val Arg Ile Ala Lys Pro Met Ala Val Glu Val Thr
            180             185             190
Tyr Asp Arg Thr Met Asn Ser Pro Asp Leu Asp Glu Thr Glu Ala Arg
            195             200             205
Met Met Phe Tyr Thr Pro Val Cys Ser Gly Pro Lys Ala Phe Thr Glu
            210             215             220
Thr Gly Tyr Arg Leu Gln Cys Ile Gln Ser Gly Arg Arg Pro Arg Leu
225             230             235             240
Met Val Val Ile Thr Met Tyr Asn Glu Asp Glu Asn Glu Leu Arg Ser
            245             250             255
Thr Leu Arg Lys Val Cys Asn Asn Val Leu Tyr Leu Lys Gln His Ser
            260             265             270
Leu Pro Gly Tyr Glu Gly Asp Asp Ala Trp Lys Gln Val Leu Val Val
            275             280             285
Val Val Ser Asp Gly Arg Thr Lys Ala Asn Lys Gly Thr Leu Glu Trp
            290             295             300
Leu Ala Asn Val Gly Leu Tyr Asp Glu Asp Val Met Asn Ile Thr Ser
305             310             315             320
Thr Gly Val Lys Val Gln Cys His Leu Phe Glu His Ser Leu Gln Met
            325             330             335
Thr Lys Glu Asn Ser Ile Arg Phe Pro Pro Leu Gln Leu Asp Ser His
            340             345             350
Leu Trp Tyr Phe Asp Ala Phe Ala Glu Gln Ile Met Pro Asp Tyr Thr
            355             360             365
Val Leu Leu Asp Val Gly Thr Met Pro Thr Lys Ser Ser Phe Tyr Lys
            370             375             380
Leu Leu Thr Ala Leu Glu Ile Asn Ala Gln Ile Gly Gly Val Cys Gly
385             390             395             400
Glu Ile Ala Val Asp Lys Pro Leu Pro Asn Met Cys Asn Trp Val Ile
            405             410             415
Ala Ala Gln His Phe Glu Tyr Lys Ile Ser Asn Ile Leu Asp Lys Ser
            420             425             430
Leu Glu Ser Cys Phe Gly Phe Ile Ser Val Leu Pro Gly Ala Phe Ser
            435             440             445
```

```
Ala Tyr Arg Tyr Lys Ala Ile Arg Gly Ala Pro Leu Gln Ala Tyr Phe
        450                 455                 460
Lys Ser Leu Thr Thr Asp Met Ala Glu Leu Gly Pro Phe Ala Gly Asn
465                 470                 475                 480
Met Tyr Leu Ala Glu Asp Arg Ile Leu Cys Phe Glu Leu Leu Ala Arg
                485                 490                 495
Lys Asp Cys Asn Trp Thr Met His Tyr Val Lys Asp Ala Ile Ala Arg
            500                 505                 510
Thr Asp Val Pro Thr Asn Leu Ile Asp Leu Val Gly Gln Arg Arg Arg
        515                 520                 525
Trp Leu Asn Gly Ser Phe Phe Ala Thr Leu Phe Ala Ile Trp Asn Trp
530                 535                 540
Gly Arg Val Tyr Thr Glu Ser Asn His Ser Leu Thr Arg Lys Leu Ala
545                 550                 555                 560
Leu Leu Val His Ala Leu Leu Gly Val Ser Ala Ala Asn Phe Tyr Leu
                565                 570                 575
Ala Leu Tyr Phe Val Ile Phe Gln Gly Phe Arg Asp Asn Arg Trp Asn
                580                 585                 590
Phe Ile Asp Thr Ser Glu Tyr Pro Gln Trp Val Leu Asp Gly Leu Pro
            595                 600                 605
Thr Ala Phe Asn Val Phe Tyr Ala Val Thr Val Phe Thr Gln Val Thr
        610                 615                 620
Ile Gly Leu Gly Asn Lys Pro Lys His Val Lys Gly Thr His Tyr Leu
625                 630                 635                 640
Ile Ser Val Leu Phe Gly Leu Leu Met Leu Leu Ala Ser Gly Val Ala
                645                 650                 655
Ile Val Ile Phe Ile Thr Ser Ser Lys Asp Ala Met Ala Ile Val Leu
            660                 665                 670
Ala Val Leu Ile Leu Gly Thr Phe Phe Ile Gly Ser Ala Leu His Cys
        675                 680                 685
Glu Val His His Ile Val Leu Thr Phe Val Gln Tyr Thr Ala Leu Met
690                 695                 700
Pro Ser Phe Val Asn Ile Leu Met Val Tyr Ser Phe Cys Asn Leu His
705                 710                 715                 720
Asp Leu Ser Trp Gly Thr Lys Gly Ile Asp Thr Gly His Glu Ala His
                725                 730                 735
Lys Thr Glu Ala Val Gly Gln Tyr Lys Asp Ile Val Ala Arg Gln Lys
            740                 745                 750
Ala Leu Glu Ala Lys Lys Ala Gln Asp Ala Arg Asn Gln Asp Glu Leu
        755                 760                 765
Lys Lys Arg Phe Asp Ser Phe Arg Ser Asn Leu Leu Leu Val Trp Val
770                 775                 780
Met Ser Asn Met Ser Met Val Ile Ile Cys Val Asn Thr Val Gly Ala
785                 790                 795                 800
Asp Ser Phe Leu Pro Phe Leu Tyr Ala Phe Val Ala Phe Asn Gly
                805                 810                 815
Ile Arg Leu Leu Gly Cys Ile Gly Tyr Leu Ile Tyr Tyr Ala Arg Gln
            820                 825                 830
Phe Leu Leu Phe Asn Thr Leu Ser Ala Thr Gly Val Leu His Lys Arg
        835                 840                 845
His Glu Ala Arg Lys His Lys Lys Ala Glu Asp Pro Asp Pro Ile Asp
850                 855                 860
```

Met Glu Leu Gly Thr Phe Asn Glu Pro Ala Thr Ser Glu Ile Gly Ala
865                 870                 875                 880

Pro Met Met Gln Ala Pro Tyr Asn Arg Met Arg
                885                 890

<210> SEQ ID NO 23
<211> LENGTH: 2880
<212> TYPE: DNA
<213> ORGANISM: Saprolegnia parasitica

<400> SEQUENCE: 23

| | | | | | |
|---|---|---|---|---|---|
| atgagcgaca | gcaacctcga | cctcgccgcc | cgcctccggg | cgctgcgcga | gggcggcgcc | 60 |
| gagcccgccc | ctgcgccggc | accgacgccc | tacatgcatt | cgccaccatc | gcggacccgg | 120 |
| cccacgccgc | tgtacacgca | agagtcgctc | gagtttggcg | ggacgtatac | gactggtagc | 180 |
| cccgtgggcg | ccgaggcgga | cggcgtgtac | acgcaggtgc | ctgtgtggaa | ggactcgaag | 240 |
| gagaagacgt | acggctactt | ggacgacgag | ccggcgccgc | aggcccagac | gctcctgaac | 300 |
| aaggccaatg | acctcgtgca | gcgccaagcc | tccaacaagg | cgtttcggcg | tcagcacaca | 360 |
| gccgcgtttc | ggccgctgcc | caacactgtc | gaggagctcc | tcgatggctc | gccgacgtac | 420 |
| gaaggcgcgt | tccggctcgt | gcagctcgcc | gtgcagatgg | agcaggatgg | cgatccgcaa | 480 |
| gccgcgatca | acttgtacgc | agacgccggc | gcgacgcttg | tcgaggtcgg | gcgcaaagaa | 540 |
| gtcgacccgc | ttttgcaaaa | gggcatccgc | caaaaggccc | aagagctcct | ccagcgtgcc | 600 |
| gaagacctcg | aggcgtggat | gaacggcgtc | gccgaggagg | cgcgcaaggc | cgctttgccg | 660 |
| ccgagcctcc | gcatcgcgcg | caccaacgtg | ccgaccgtcg | agcagacgtg | ggccggccga | 720 |
| ccgccgccct | ccatgacgcg | caacgaattc | aaattgatgc | ggtacacggc | ggtggcgacc | 780 |
| aaggacccga | tccagttctc | ggacgacggc | tacgtgctcc | gcgtgcacga | gctgcaacga | 840 |
| cccatcaagg | tctttatcac | gatcaccatg | tacaacgaag | aaggctcgga | gatcaagggc | 900 |
| acgctcacgg | gccttgccaa | aggtctcgcg | tacatgtgca | aggagtacgg | cgacgacttt | 960 |
| tggcagcaag | tcgcggtggc | catcgtctcg | gacggccgga | cgaaagcgtc | caagacgtgt | 1020 |
| ctcgagtacc | tcaaggccgt | cggcgcgttt | gacgaagaga | tcatgacggt | cacgtcgctc | 1080 |
| ggtgtcgacg | tccagatgca | tctcttcgag | tcgacgctcc | agctggtcga | gaaccagaac | 1140 |
| tttgaggcct | attcccacc | gctgcaagtg | atttacgcgc | tcaaggagaa | caatggcggg | 1200 |
| aagctcaact | cgcatctctg | gttcttcaac | gcgttctcgg | agcagctcaa | cccaaagtac | 1260 |
| acggtgctcg | tcgacgtcgg | gacgattccc | gccgagacct | cggtctttcg | cttgatccgg | 1320 |
| agcatggagc | gcaacgcgca | gattggcggt | gtcgctggcg | agattgcagt | tgaagccccg | 1380 |
| aatttcttca | accctgtgat | tgccgcccag | catttcgagt | acaagatctc | caacattatg | 1440 |
| gacaagtcgc | tcgagtcggt | gttggctttt | atctcggtgc | tgcccggtgc | gttctcagcg | 1500 |
| taccggtacg | aagcgattcg | ggccgtcaag | ggcgtcgggc | cgctgcccga | gtactttaaa | 1560 |
| agcctcacgt | cgacgaccaa | ggagctcggg | ccgttccaag | gcaacatgta | cttggccgaa | 1620 |
| gaccgcatct | tgtgctttga | gctcctcgcg | cgcaagcagc | ggcgctggac | catgcactac | 1680 |
| gtcaaggacg | cgattgcgcg | cacggacgtg | cccgaaacgc | tcgtcgacct | catcaagcag | 1740 |
| cgccggcgct | ggctcaacgg | gtcgttcttc | gcgggcctct | ttgcgatcgg | gcactttggc | 1800 |
| cgcgtctgga | gccaaagcag | ccactcgttt | ggtcgcaagc | tcgtgtttac | gttccagttt | 1860 |
| gtctacctcg | cgctccagaa | cctcctctcg | tggtttctgt | tgagcaacct | cttttctgacg | 1920 |
| ttttactttg | tcttgacgct | ggcctttacc | gagtcggcgc | cggcgctgct | ccagacgatg | 1980 |

```
ctgaccgtct acctcgcgat cattggcggc ctcatcgtct ttgcccttgg caacaagccc      2040
gagccgcgca cggccagctt ttacctcttt agctgcctct acatgggcat catcatgctg      2100
ctcgtgacgg gcatttccat ctacggcttg attggcaagg gtacgagcgc cgtcaaggac      2160
ccgcgcacga tcaccgggat cttctccaac tgcacggtca gcgacgccga gctcgcgggc      2220
ggcgtcatca cgtcgctcgg gctcatcttc ctctcggcct tcgtccacgg cgagtttggc      2280
atcctcctca gctttgtgca gtatttcttc atgctcccga cgtttgtcaa cgtgctgggc      2340
atctatgcgt acagcaacct tcatgatctg agctggggca cgaaaggcct cgagtcgggc      2400
ggcggccacg ggcccgccaa ggccggcggc ggcaacgtca aggacgtcgt cgagcagcaa      2460
aagaagatag aggccgcgcg gcaagccgcc gccagagaga aggaagatgt cgacaacagc      2520
ttccgcgcgt tccggtcgac gttgctgctc tcgtggctca cgaccaacgg catttggctg      2580
tacgtcgtca cggactacat gtcgagcggg tgctacctca agggcctcag ctacattgtc      2640
ggcttcttca cgtcgtgcg ctttacgggc tgcgtcgtgt ttgtgatcct gcgcatgttt      2700
cggcggttcg gctgcggcgc gcgcgcgtcc cgcgacaact accaagaggc gctgccggcc      2760
gagtggcaga cgcactacaa cgtgacgaac cgaaccgatg ccgcgtcgc gccgccgccc      2820 aagcacgcgg cgtcgatgga cccgaccacg ccccatggcg gcgtctacca gcaagtgtaa      2880
```

<210> SEQ ID NO 24
<211> LENGTH: 959
<212> TYPE: PRT
<213> ORGANISM: Saprolegnia parasitica

<400> SEQUENCE: 24

```
Met Ser Asp Ser Asn Leu Asp Leu Ala Ala Arg Leu Arg Ala Leu Arg
1               5                   10                  15

Glu Gly Gly Ala Glu Pro Ala Pro Ala Pro Thr Pro Tyr Met
            20                  25                  30

His Ser Pro Ser Arg Thr Arg Pro Thr Pro Leu Tyr Thr Gln Glu
        35                  40                  45

Ser Leu Glu Phe Gly Gly Thr Tyr Thr Thr Gly Ser Pro Val Gly Ala
50                  55                  60

Glu Ala Asp Gly Val Tyr Thr Gln Val Pro Val Trp Lys Asp Ser Lys
65                  70                  75                  80

Glu Lys Thr Tyr Gly Tyr Leu Asp Asp Glu Pro Ala Pro Gln Ala Gln
                85                  90                  95

Thr Leu Leu Asn Lys Ala Asn Asp Leu Val Gln Arg Gln Ala Ser Asn
            100                 105                 110

Lys Ala Phe Arg Arg Gln His Thr Ala Ala Phe Arg Pro Leu Pro Asn
        115                 120                 125

Thr Val Glu Glu Leu Leu Asp Gly Ser Pro Thr Tyr Glu Gly Ala Phe
    130                 135                 140

Arg Leu Val Gln Leu Ala Val Gln Met Glu Gln Asp Gly Asp Pro Gln
145                 150                 155                 160

Ala Ala Ile Asn Leu Tyr Ala Asp Ala Gly Ala Thr Leu Val Glu Val
                165                 170                 175

Gly Arg Lys Glu Val Asp Pro Leu Leu Gln Lys Gly Ile Arg Gln Lys
            180                 185                 190

Ala Gln Glu Leu Leu Gln Arg Ala Glu Asp Leu Glu Ala Trp Met Asn
        195                 200                 205

Gly Val Ala Glu Glu Ala Arg Lys Ala Ala Leu Pro Pro Ser Leu Arg
```

```
            210                 215                 220
Ile Ala Arg Thr Asn Val Pro Thr Val Glu Gln Thr Trp Ala Gly Arg
225                 230                 235                 240

Pro Pro Pro Phe His Asp Ala Asn Glu Phe Lys Leu Met Arg Tyr Thr
                245                 250                 255

Ala Val Ala Thr Lys Asp Pro Ile Gln Phe Ser Asp Asp Gly Tyr Val
                260                 265                 270

Leu Arg Val His Glu Leu Gln Arg Pro Ile Lys Val Phe Ile Thr Ile
                275                 280                 285

Thr Met Tyr Asn Glu Glu Gly Ser Glu Ile Lys Gly Thr Leu Thr Gly
            290                 295                 300

Leu Ala Lys Gly Leu Ala Tyr Met Cys Lys Glu Tyr Gly Asp Asp Phe
305                 310                 315                 320

Trp Gln Gln Val Ala Val Ala Ile Val Ser Asp Gly Arg Thr Lys Ala
                325                 330                 335

Ser Lys Thr Cys Leu Glu Tyr Leu Lys Ala Val Gly Ala Phe Asp Glu
                340                 345                 350

Glu Ile Met Thr Val Thr Ser Leu Gly Val Asp Val Gln Met His Leu
            355                 360                 365

Phe Glu Ser Thr Leu Gln Leu Val Glu Asn Gln Asn Phe Glu Ala Tyr
370                 375                 380

Tyr Pro Pro Leu Gln Val Ile Tyr Ala Leu Lys Glu Asn Asn Gly Gly
385                 390                 395                 400

Lys Leu Asn Ser His Leu Trp Phe Phe Asn Ala Phe Ser Glu Gln Leu
                405                 410                 415

Asn Pro Lys Tyr Thr Val Leu Val Asp Val Gly Thr Ile Pro Ala Glu
                420                 425                 430

Thr Ser Val Phe Arg Leu Ile Arg Ser Met Glu Arg Asn Ala Gln Ile
                435                 440                 445

Gly Gly Val Ala Gly Glu Ile Ala Val Glu Ala Pro Asn Phe Phe Asn
                450                 455                 460

Pro Val Ile Ala Ala Gln His Phe Glu Tyr Lys Ile Ser Asn Ile Met
465                 470                 475                 480

Asp Lys Ser Leu Glu Ser Val Phe Gly Phe Ile Ser Val Leu Pro Gly
                485                 490                 495

Ala Phe Ser Ala Tyr Arg Tyr Glu Ala Ile Arg Ala Val Lys Gly Val
                500                 505                 510

Gly Pro Leu Pro Glu Tyr Phe Lys Ser Leu Thr Ser Thr Lys Glu
                515                 520                 525

Leu Gly Pro Phe Gln Gly Asn Met Tyr Leu Ala Glu Asp Arg Ile Leu
530                 535                 540

Cys Phe Glu Leu Leu Ala Arg Lys Gln Arg Arg Trp Thr Met His Tyr
545                 550                 555                 560

Val Lys Asp Ala Ile Ala Arg Thr Asp Val Pro Glu Thr Leu Val Asp
                565                 570                 575

Leu Ile Lys Gln Arg Arg Trp Leu Asn Gly Ser Phe Phe Ala Gly
                580                 585                 590

Leu Phe Ala Ile Gly His Phe Gly Arg Val Trp Ser Gln Ser Ser His
                595                 600                 605

Ser Phe Gly Arg Lys Leu Val Phe Thr Phe Gln Phe Val Tyr Leu Ala
            610                 615                 620

Leu Gln Asn Leu Leu Ser Trp Phe Leu Leu Ser Asn Leu Phe Leu Thr
625                 630                 635                 640
```

-continued

```
Phe Tyr Phe Val Leu Thr Leu Ala Phe Thr Glu Ser Ala Pro Ala Leu
                645                 650                 655

Leu Gln Thr Met Leu Thr Val Tyr Leu Ala Ile Ile Gly Gly Leu Ile
            660                 665                 670

Val Phe Ala Leu Gly Asn Lys Pro Glu Pro Arg Thr Ala Ser Phe Tyr
        675                 680                 685

Leu Phe Ser Cys Leu Tyr Met Gly Ile Ile Met Leu Leu Val Thr Gly
    690                 695                 700

Ile Ser Ile Tyr Gly Leu Ile Gly Lys Gly Thr Ser Ala Val Lys Asp
705                 710                 715                 720

Pro Arg Thr Ile Thr Gly Ile Phe Ser Asn Cys Thr Val Ser Asp Ala
                725                 730                 735

Glu Leu Ala Gly Gly Val Ile Thr Ser Leu Gly Leu Ile Phe Leu Ser
            740                 745                 750

Ala Phe Val His Gly Glu Phe Gly Ile Leu Leu Ser Phe Val Gln Tyr
        755                 760                 765

Phe Phe Met Leu Pro Thr Phe Val Asn Val Leu Gly Ile Tyr Ala Tyr
    770                 775                 780

Ser Asn Leu His Asp Leu Ser Trp Gly Thr Lys Gly Leu Glu Ser Gly
785                 790                 795                 800

Gly Gly His Gly Pro Ala Lys Ala Gly Gly Gly Asn Val Lys Asp Val
                805                 810                 815

Val Glu Gln Gln Lys Lys Ile Glu Ala Ala Arg Gln Ala Ala Ala Arg
            820                 825                 830

Glu Lys Glu Asp Val Asp Asn Ser Phe Arg Ala Phe Arg Ser Thr Leu
        835                 840                 845

Leu Leu Ser Trp Leu Thr Thr Asn Gly Ile Trp Leu Tyr Val Val Thr
    850                 855                 860

Asp Tyr Met Ser Ser Gly Cys Tyr Leu Lys Gly Leu Ser Tyr Ile Val
865                 870                 875                 880

Gly Phe Phe Asn Val Val Arg Phe Thr Gly Cys Val Val Phe Val Ile
                885                 890                 895

Leu Arg Met Phe Arg Arg Phe Gly Cys Gly Ala Arg Ala Ser Arg Asp
            900                 905                 910

Asn Tyr Gln Glu Ala Leu Pro Ala Glu Trp Gln Thr His Tyr Asn Val
        915                 920                 925

Thr Asn Arg Thr Asp Gly Arg Val Ala Pro Pro Lys His Ala Ala
    930                 935                 940

Ser Met Asp Pro Thr Thr Pro His Gly Gly Val Tyr Gln Gln Val
945                 950                 955
```

METHODS FOR MANUFACTURING PLANT CELL WALLS COMPRISING CHITIN

FIELD OF THE INVENTION

The present invention relates to the modification of the reactivity of plant cell walls such as secondary plant cell walls. In particular, the present invention provides cotton fibers comprising positively charged polysaccharides such as chitin and chitosan. These cotton fibers have a modified reactivity which can be exploited for dyeing the fibers with fiber-reactive dyes. In addition, the modified reactivity can be applied to improve the reactivity of the fibers with reactants such as flame retardants, water, oil and soil repellents, softeners, antistatic agents, fluorescent whitening agents and the like.

INTRODUCTION TO THE INVENTION

Mankind has been using natural fibers, including cellulose containing natural fibers from plants, such as cotton and linen, for several thousand years to produce many different kinds of textiles. With increasing demand and improved fiber quality, a global textile industry based on cotton developed rapidly. Today, cotton contributes approximately 45 percent to the world's clothing, and many of the best fashion houses use textiles made from high quality cotton. Cotton fiber consists of cellulose, a natural polymer composed of many molecules of the sugar glucose. Its unique structure is ideally suited for textile production. Each fiber is basically a hollow tube a few centimeters in length that, when spun and woven, provides the very special characteristic "feel" of cotton. Natural cellulose containing fibers, however, do not possess the chemical versatility of synthetic fibers, due to the relative inert nature of the cellulose consisting of β-1-4 linked glucose monomers. This relatively inert nature is apparent during the dyeing process of cotton fibers and fabrics. Direct dyes and fiber-reactive dyes are two types of anionic dyes used to color cotton. Cotton itself develops an anionic charge in water, so that without special treatment, the uptake of dye by the fiber or fabric is quite elaborate. Direct dyes create a relatively weak hydrogen bond with the cellulose polymer forming a semi-permanent attachment because it does not withstand well washing. Fiber-reactive dyes are molecules that combine chromophores with a reactive group that forms strong covalent bonds with the fiber via reaction with hydroxyl groups. The covalent bonds provide a good resistance of the dyed fiber against laundring. During the dyeing process, large amounts of electrolytes are needed to shield the anionic dyes from the anionic fiber charges. Unreacted hydrolyzed dyes (up to 40%) need to be removed by a washing step, generating large volumes of wastewater, also containing the above mentioned electrolytes.

Providing the cellulose fiber with a positive electric charge, e.g. by incorporation of positively charged chemical compounds, could therefore improve the dyeability of natural cellulose fibers, as well as improve any chemical reaction of the modified cellulose fiber with negatively charged chemical compounds. It would also make the use of acidic dyes possible.

Several publications have described the coating of chitosan oligomers onto cellulose fibers to make chitosan/cellulose blends, yarns or fabrics. Chitosan is a positively charged polymer of glucosamine, which can be obtained by deacetylation of chitin, e.g. by alkaline treatments. Chitin itself is a polymer of β-1-4 linked N-acetylglucosamine (GlcNAc).

Liu et al. (*Carbohydrate Polymers* 44(2003) 233-238) described a chemical method for surface coating cotton fibers with chitosan. With this chitosan coating, the cotton fiber surface became physiologically and biologically active because of the chemical reactivity of the amino group leading to a higher potential for subsequent chemical modification of the fibers. Based on the physiological function of chitosan in inhibiting e.g. dermatophytes, many functional clothes, fabrics and fibers employ cellulose-chitosan blend fibers, cellulose fiber-chitosan conjugate and fabrics coated with chitosan-containing resins.

WO 00/09729 describes the expression of chitin synthase and chitin deacetylase genes in plants to alter the cell wall for industrial uses and improved disease resistance. Specifically cited uses are: to provide a single plant source of cellulose, chitin and chitosan, to increase tensile strength and to increase brittle snap. Specifically suggested chitin synthase genes are derived from fungal organisms. Experimental data are neither provided on the production of chitin or chitosan in plants, nor on the incorporation thereof in plant cell walls. WO2006/136351 showed that the strategy as proposed in WO00/09729 does not lead to the functional incorporation of chitin into the plant cell wall. Instead WO 2006/136351 discloses that chitin is effectively produced in the secondary cell wall of cotton fibers only when the fungal chitin synthase (from *Neurospora crassa*) is actively relocated to the Golgi apparatus. The latter is achieved by operable fusion of this fungal chitin synthase with a signal anchor sequence specific for the Golgi apparatus, and by expressing the resulting chimeric gene in plants. Although, chitin could be efficiently produced in cotton plant cell walls it was also observed that the transgenic plants remained smaller presumably due to toxicity of the expression of the chimeric chitin synthase in cotton outside of the cotton fibers.

Thus there remains a need for alternative methods to produce plant cell walls such as secondary cell walls which comprise positively charged polysaccharides. In particular a need exists for providing methods to produce fibers which can be directly harvested from plants and which contain positively charged chemical groups and/or group which are more reactive than hydroxyl groups of cellulose, which can be used directly without the need for further chemical treatment to introduce such chemical groups and wherein the transgenic plants do not show a growth retardation. These and other problems are solved as described hereinafter in the different embodiments, examples and claims.

SUMMARY OF THE INVENTION

The invention shows that the expression of a chitin synthase derived from *Saprolegnia monoica*, which is not operably linked with a Golgi targeting signal, in plant cells leads to the efficient incorporation of N-acetylglucosamine polymers in the plant cell wall, in particular the plant secondary cell wall. The invention described herein in the different embodiments, examples, and claims provides *Saprolegnia* chitin synthases and chimeric genes thereof comprised in expression cassettes which can be used to modify the plant cell walls with positively charged polysaccharides. Accordingly, the invention provides in a first object an isolated nucleic acid molecule comprising a nucleotide sequence which encodes a chitin synthase polypeptide wherein said nucleotide sequence is at least 97% identical to SEQ ID NO: 1 or a complementary sequence thereof. In another embodiment the invention provides an isolated nucleic acid molecule comprising a nucleotide sequence which encodes a chitin synthase polypeptide which is at least 80% identical to SEQ ID NO: 2. In yet another embodiment the invention provides a chimeric gene comprising the following operably linked DNA regions a) a plant-expressible promoter, b) a nucleotide sequence which is at least 97% identical to SEQ ID NO: 1 or a complementary sequence thereof or a nucleotide sequence which encodes a chitin synthase polypeptide which is at least 80% identical to SEQ ID NO: 2 and c) a transcription termination and polyadenylation region. In yet another embodiment the chimeric gene comprises a constitutive promoter. In yet another embodiment the chimeric gene comprises a fiber-selective promoter. In yet another embodiment the chimeric gene comprises an expansin promoter. In yet another embodiment the invention provides a chimeric gene as defined in any of the previous embodiments. In yet another embodiment the invention provides a plant consisting essentially of a plant cell comprising a chimeric gene as defined in any of the previous embodiments. In a particular embodiment the plant is a cotton plant. In yet another embodiment the invention provides fibers obtained from the plant according to the invention. In yet another embodiment the invention provides a transgenic seed comprising a chimeric gene as defined in any of the previous embodiments. In yet another embodiment the invention provides a method for the manufacture of a plant cell wall comprising positively charged polysaccharides, said method comprises expressing a chimeric gene according to any of the previous embodiments in a plant and isolating said plant cell wall. In a particular embodiment said method provides a cotton plant cell wall. In yet another particular embodiment said method provides a cotton plant cell wall which is present in a cotton fiber.

FIGURE

Figure 1B:
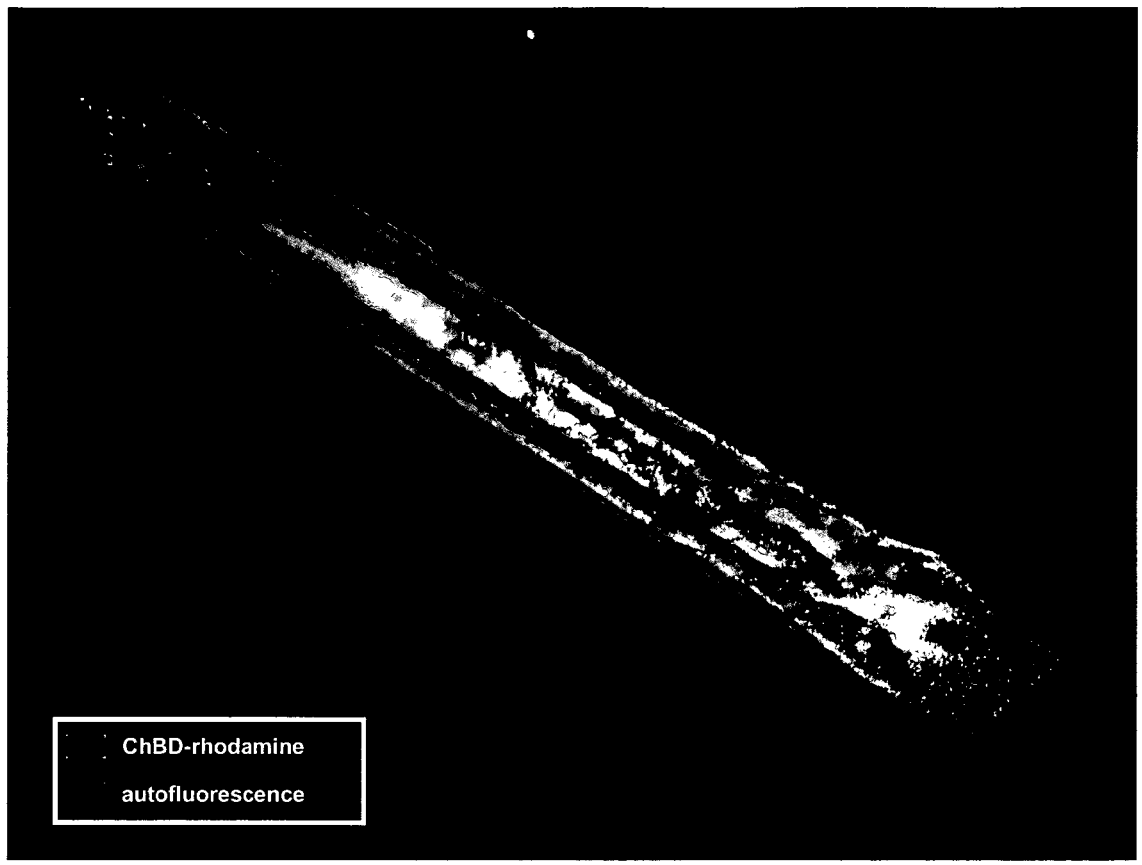

FIG. 1:

FIG. 1a shows untransformed mature trichomes (*Arabidopsis thaliana*) which are stained with a rhodamine-conjugated chitin-binding probe while FIG. 1b shows recombinant mature trichomes (*Arabidopsis thaliana*) comprising the SmCHS2 chimeric gene stained with a rhodamine-conjugated chitin-binding probe. A clear reaction with the chitin binding probe is observed since the recombinant trichomes (FIG. 1b) are stained more intensively than trichomes derived from control plants (FIG. 1a). Chitin is witnessed by the presence of red dots in the recombinant trichomes (FIG. 1b) while the red dots are absent in the untransformed trichomes (FIG. 1a).

DETAILED DESCRIPTION OF DIFFERENT EMBODIMENTS OF THE INVENTIONS

The current invention hinges on the remarkable finding that expression of the *Saprolegnia monoica* gene coding for a chitin synthase in plant cells leads to the efficient incorporation of N-acetylglucosamine (GlcNAc) polymers into plant cell walls. The *Saprolegnia monoica* gene coding for a chitin synthase does not require to be operably linked (or fused) with a Golgi targeting localisation signal as was required with the *Neurospora crassa* chitin synthase in WO2006/136351. In the present invention it was observed that chitin (i.e. a polymer of N-acetylglucosamine) was made in the cell wall, in particular the secondary cell wall, of the transgenic plants. The *Saprolegnia monoica* gene coding for a chitin synthase can be used e. g. for expression in cotton plants for the generation of more reactive cotton fibers.

Thus the invention provides in a first embodiment an isolated nucleic acid molecule comprising a nucleotide sequence which encodes a chitin synthase polypeptide wherein said nucleotide sequence is at least 97% identical to SEQ ID NO: 1 or a complementary sequence thereof. SEQ ID NO: 1 depicts the nucleotide sequence of the *Saprolegnia monoica* chitin synthase 2 (SmCHS2).

In another embodiment the invention provides an isolated nucleic acid molecule comprising a nucleotide sequence which encodes a chitin synthase polypeptide which is at least 80% identical to SEQ ID NO: 2. SEQ ID NO: 2 depicts the amino acid sequence of the *Saprolegnia monoica* chitin synthase 2 (SmCHS2). In a specific embodiment the invention provides an isolated nucleic acid molecule comprising a nucleotide sequence which encodes a chitin synthase polypeptide which is at least 85%, at least 90%, at least 95% or at least 98% or even at least 99% identical to SEQ ID NO: 2. In yet another embodiment the invention provides an isolated nucleic acid molecule comprising a nucleotide sequence which encodes a chitin synthase polypeptide wherein said nucleotide sequence is at least 90% identical to SEQ ID NO: 3 or a complementary sequence thereof. In a specific embodiment the invention provides an isolated nucleic acid molecule comprising a nucleotide sequence which encodes a chitin synthase polypeptide wherein said nucleotide sequence is at least 95%, at least 98 or even at least 99% identical to SEQ ID NO: 3 or a complementary sequence thereof. SEQ ID NO: 3 is the *Saprolegnia monoica* chitin synthase 1 (SmCHS1). In yet another embodiment the invention provides an isolated nucleic acid molecule comprising a nucleotide sequence which encodes a chitin synthase polypeptide which is at least 80% identical to SEQ ID NO: 4. In a specific embodiment the invention provides an isolated nucleic acid molecule comprising a nucleotide sequence which encodes a chitin synthase polypeptide which is at least 85%, at least 90% identical, at least 95%, at least 98% or even at least 99% identical to SEQ ID NO: 4. SEQ ID NO: 4 is the amino acid sequence of the *Saprolegnia monoica* chitin synthase 1.

Nucleic acids can be DNA or RNA, single- or double-stranded. Nucleic acids can be synthesized chemically or produced by biological expression in vitro or even in vivo. Nucleic acids can be chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

In connection with the chimeric gene of the present disclosure, DNA includes cDNA and genomic DNA.

In enzymology, a chitin synthase (EC 2.4.1.16) is an enzyme that catalyzes the chemical reaction:

UDP-N-acetyl-D-glucosamine+[1,4-(N-acetyl-beta-D-glucosaminyl)]n→UDP+[1,4-(N-acetyl-beta-D-glucosaminyl) ]n+1

Thus, the two substrates of this enzyme are UDP-N-acetyl-D-glucosamine and [[[1,4-(N-acetyl-beta-D-glucosaminyl)]n]], whereas its two products are UDP and [[[1,4-(N-acetyl-beta-D-glucosaminyl)]n+1]]. This enzyme belongs to the family of glycosyltransferases, specifically the hexosyltransferases. The systematic name of this enzyme class is UDP-N-acetyl-D-glucosamine:chitin 4-beta-N-acetylglucosaminyl-transferase. Other names in common use include chitin-UDP N-acetylglucosaminyltransferase, chitin-uridine diphosphate acetylglucosaminyltransferase, chitin synthetase, chitin synthase and trans-N-acetylglucosaminosylase. This enzyme participates in aminosugars metabolism. Thus chitin is a polymer of beta-1,4-linked N-acetyl-D-glucosamine (GlcNAc)

The chitin synthases 1 and 2 (respectively depicted in SEQ ID NO: 3 and 1) are derived from *Saprolegnia monoica*. The genus *Saprolegnia* belongs to the family of Oomycetes. Based on their general morphology and lifestyles, this group was traditionally classified as fungi. However, a cladistic classification based on modern insights, supports a relatively close relationship with the photosynthetic organisms such as brown algae and diatoms, within the eukaryotic group—the heterokonts. The sequences of the chitin synthases 1 and 2 derived from *S. monoica* comprise a conserved aminoterminal domain of approximately 70 amino acids, also known as a MIT domain. A MIT domain is a conserved domain comprising approximately 70 amino acids, with alternating conserved hydrophobic and polar areas and a predicted helical secondary structure first identified in proteins involved in microtubule binding and in intracellular transport. Such a domain is designated as a MIT domain (contained within Microtubule Interacting and Trafficking molecules). The MIT domain is also found in sorting nexins, the nuclear thiol protease PalBH, the AAA protein spastin and archaebacterial proteins with similar domain architecture, vacuolar sorting proteins and others. The precise molecular function of the MIT domain is unclear. Without intending to limit the invention to a particular mode of action, it is thought that the MIT domain present in the chitin synthases of *S. monoica* is responsible for the efficient synthesis of chitin in the cell walls of transgenic plants. It was previously shown in WO2006/136351 that chitin synthases of fungal origin (such as a *Neurospora crassa* chitin synthase) had to be adapted by means of operable coupling of the fungal chitin synthase with a Golgi localisation signal, to obtain for efficient synthesis of chitin in the cell wall of transgenic plants. Since a MIT domain is present in a few other chitin synthases, in particular in some chitin synthases derived from oomycetes, the invention provides the use of chitin synthases naturally comprising an MIT domain for the manufacture of chitin in the plant secondary cell wall. Such chitin synthases naturally comprising an MIT domain include those of *Saprolegnia parasitica* having the amino acid sequence depicted in SEQ ID NO: 22 and SEQ ID NO: 24 or encoded by the nucleic acid sequences depicted in SEQ ID NO: 21 and SEQ ID NO: 23.

In another embodiment the invention provides the operable coupling of a MIT domain with a chitin synthase, such as a fungal chitin synthase, not comprising an MIT domain, e. g. a non-oomycete chitin synthase to generate a chimeric chitin synthase for efficient production of chitin in the plant secondary cell wall. In other words, disclosed is a chimeric gene comprising a DNA region coding for a chitin synthase polypeptide not comprising an MIT domain operably linked to a DNA region encoding an MIT domain such that, upon expression, a fusion protein is made, a plant expressible promoter and a transcription termination and polyadenylation region. Also disclosed is a method for the manufacture of a plant cell wall comprising positively charged polysaccharides comprising a) expressing a chimeric gene comprising a DNA region coding for a chitin synthase polypeptide not comprising an MIT domain operably linked to a DNA region encoding an MIT domain such that, upon expression, a fusion protein is made, a plant expressible promoter and a transcription termination and polyadenylation region; and b) isolating the plant cell wall obtained in a).

MIT domains have been assigned the Pfam family number PF04212. Currently, 495 proteins are known which are known or predicted to comprise an MIT domain. The sequences of these proteins can be retrieved e. g. from the UniProt server on the world wide web at uniprot.org/) under the following UniProt accession numbers which are followed by the position of the (predicted) MIT domain within the sequence. Sequences and in particular that of the (predicted) MIT domains are described in the art as follows:

C5L7B3/6-74; C5K7I8/6-74; B9PJ69/9-77; B6K9M2/9-77; B9QA65/9-77; A7ASR9/7-74; B6AJD9/4-72; Q5CFS7/1-69; Q5CSB4/3-71; Q4UC87/4-82; B3L9J0/6-74; A5K3I1/6-74; Q8IKQ5/6-74; Q4Z291/6-74; Q4X5E3/6-74; Q7RRP6/6-74; A8IAJ1/7-74; Q6ETH5/5-73; B8AI60/5-73; B9SG62/5-73; B9HVY7/5-73; B9HL02/5-73; B9NGD1/5-73; Q3EDG2/1-41; Q9SGD4/1-41; Q8LKV4/5-73; B6TLN7/5-73; B8A2I4/5-73; B6T3Y2/5-73; A2WKH8/5-73; A2ZP36/5-73; B8A2W9/5-73; A2WKI0/5-73; Q5ZEN9/5-73; Q8LAK9/5-73; Q9ZNT0/5-73; Q9SEA8/5-73; Q1W2L1/5-73; B9HQW8/5-73; B9H1R8/5-73; A5BIG1/5-73; A7R0D5/5-73; A9SGM2/5-73; A9TBU2/5-73; A9P2N1/5-73; B9SCR4/5-73; A4S3E8/8-75; C1ECR7/11-78; C1NA06/11-78; C1E2F1/103-169; B6K5C2/6-74; Q09803/6-74; A8PSV3/1-33; Q5KC30/6-74; Q4PDZ4/6-74; A8N0F3/6-74; B0DXQ0/6-74; A7F3H9/6-74; Q7S0H4/6-74; Q2GQ74/6-74; B2AFE6/6-74; C5FLK6/6-74; C5JDP2/6-74; C5GXE6/6-74; C0NGS1/6-74; C0SHS5/6-74; C1H9G7/6-74; C1GCX1/6-74; C4JW95/6-74; Q1E6C4/6-74; B6QQZ4/6-74; B8M727/6-74; Q2UQD2/6-74; B8MZP8/6-74; A1D7B7/7-75; B0XY62/7-75; Q4WXF8/7-75; Q5B8R9/6-74; Q0CXN9/6-74; B6GYF9/6-74; A2R7C1/6-74; A1CK47/6-74; B2VXZ4/6-65; Q0U7R6/6-74; Q6CEE2/6-74; Q5YKJ0/7-75; C4R134/4-72; Q6FQG5/6-74; Q9C1F4/6-74; B3LKD3/6-74; A6ZX48/6-74; P52917/6-74; B5VTV5/1-34; C5DUT4/6-74; Q6CVM8/6-74; C5DBA6/6-74; A7TH89/6-74; Q758U9/6-74; C4Y9U8/7-75; Q5AGH7/7-75; Q5AG40/7-75; B9WHM5/7-75; A5E2L0/55-123; C5MHK4/5-73; A5DQ68/6-74; A3LVF1/7-75; Q6BPY2/7-75; A9V5Z2/5-73; Q57V58/5-74; Q4E658/5-74; Q4D9C2/5-74; Q4FXF2/5-74; A4I4W4/5-74; A4HHP9/5-74; Q54PT2/6-74; Q4RKZ3/1-69; A8QBQ7/7-76; C3YEH0/5-74; C3ZYE4/31-98; C4Q408/2-71; Q5DBH6/2-71; A8Y1H3/5-74; Q9BL83/5-74; B3RJ28/5-74; A7SK75/5-74; B3MXW2/6-75; Q29H77/6-75; B4NPI4/6-75; B4L2B2/6-75; B3NWZ3/6-75; B4M6S6/6-75; B4R6Q7/6-75; B4I6L5/6-75; Q9Y162/6-75; B4Q2M1/6-75; Q7QFR0/6-75; B0XJH8/6-75; Q17GP3/6-75; B7PVD7/6-75; Q66IY7/5-74; B2GUK1/3-72; B2RCB7/5-74; Q9UN37/5-74; Q08BZ6/5-74; Q4SKA0/1-69Q2HJB1/5-74; Q793F9/5-74; Q8VEJ9/5-74; Q6IRG3/5-74; Q3TDX2/5-74; Q5U4Y4/7-76; Q6DJK7/7-76; Q8AVB9/7-76; B5X7N1/5-74; VPS4B/7-76; A8K4G7/7-76; Q69HW4/7-76; A8K5D8/7-76; O75351/7-76; Q3TN07/7-76; Q6PJZ4/7-76; P46467/7-76; Q4KLL7/7-76; Q3U8P5/7-76; Q0VD48/7-76; Q4RVG5/6-75; Q5ZMI9/4-73; C0H991/95-164; B5X1U4/6-75; Q7SXY0/6-75; A7YYH5/6-75; B2GU12/6-75; A5WWM0/6-75; C0H991/9-78; Q8T127/7-75; B7P0K9/283-324; C3Z907/321-389; A7S4I8/283-324; Q4S8A8/285-352; A4IG43/277-345; A4IID6/279-347; Q4V7Q6/279-347; Q5ZJH6/280-348; B4DFS6/190-258; B4DRQ7/280-348; B2RXK3/280-348; B4DDG2/163-231; B4DQN3/163-231; B4DFT0/291-359; Q3U3Q1/280-348; B2RXB9/280-348; B3RSI2/276-344; B4GNS6/275-343; Q29BD1/275-343; B4NAJ4/275-343; B3M073/275-343; Q86P98/275-343; Q8T0L6/275-343; Q9VHF6/275-343; B3P1R41275-343; B4QX75/275-343; B4HKF5/275-343; B4PUL9/275-343; B4K4Y3/275-343; B4LW06/275-343; B4JYT0/275-343; B0XAE0/178-246; Q7QEQ2/275-343; Q5C1I1/163-221; C4Q8U0/273-338; B0E7C2/4-72; C4LYN8/4-72; A3DP09/6-74; B8D2W2/9-77; A9A4K6/8-76; B3TCM2/8-75; A0RVT9/8-75; Q877H3/7-75; Q972B3/7-75; Q97ZJ7/7-75; C3MPU4/7-75; C3NE34/7-75; C3NHM9/7-75; C4KH36/7-75; C3MUV6/7-75; C3N5H0/7-75; A4YHC5/7-75;

A2BKZ1/9-75; Q9YDF3/7-75; C4LZH7/3-71; A8BSU6/8-77; Q8T6L4/8-77; B8C9Z5/5-73; B8LDI1/5-73; B7GCY6/5-73; Q54CX7/4-72; Q22143/5-70; A8XST3/5-70; Q54CX7/246-316; Q55GN8/5-73; A4QZC1/8-77; A2D8M7/10-80; Q54RJ5/10-79; C4LYH7/2-70; Q8I8X1/16-84; Q54CX7/120-188; Q0UZT0/375-444; C4JEZ5/18-85; Q1E904/19-86; C5FCB8/23-90; C1GDJ4/63-130; C0SAK1/19-86; C1HDA2/19-86; C5JPG7/78-145; C5G855/19-86; A6RHR0/1-68; C0NMG2/1-68; A2QKF2/239-307; B6H2K6/100-168; Q0CFY4/216-284; B0XW44/210-278; A1DG63/193-261; Q4X270/211-279; A1CSH7/266-334; B8NC13/82-150; Q2TZ95/233-301; Q5B0X3/178-246; B8M0Z2/44-113; B6Q8T3/44-113; A7EZ31/1-69; A6S2Q3/293-361; Q7S0P7/402-470; B2ADU1/368-424; Q2GTY0/352-420; C1E4H7/3-68; C1MPZ7/3-69; C3ZZL4/6-70; B7P5B6/8-73; Q9R1S8/6-71; Q499T5/6-71; Q9Y6W3/6-71; B2RAM2/6-71; Q7Z479/6-71; A0FKG7/6-71; B0FGU2/6-71; B4F6P1/6-71; C0H9M1/6-71; Q4S467/6-71; B3RQK1/8-73; A7RRP7/7-70; Q54JG4/13-81; Q55GN8/176-244; C4LYH7/369-438; Q8I8X1/383-452; B0EV39/371-440; A9V3C1/6-74; A7URZ9/6-72; B0X0P8/1-69; Q16FL8/1-69; Q0IFG1/1-69; B4KNS6/15-76; B4MS07/21-82; B3M8E0/5-71; B4IZ41/4-72; B4KXT1/5-71; B4MFW3/3-71; B4MLA7/3-71; Q29EY7/4-71; B3NG09/3-71; B4PH91/3-71; Q9VZK1/3-71; Q7YU93/3-71; B4QQ18/3-62; B4HTX3/3-71; B3RKL7/450-515; Q7T332/322-390; A9JT54/322-390; A4IIB7/268-336; Q28CB9/261-329; Q63ZH0/269-337; Q0P3R2/270-338; A7SVK8/274-341; Q20821/252-320; A8Y3X4/266-339; Q148E7/275-343; B3KU31/268-336; B2RDR2/268-336; Q9NRS6/268-336; B0CM75/268-336; Q4V896/269-337; Q91WE1/268-336; Q9CW22/63-131; Q6NU31/257-325; KS6C1/239-307; B1APS8/227-295; B3KVM4/239-307; B4DRK0/58-126; Q5R5U6/239-307; KS6C1/238-306; B8JLT3/232-300; Q4RR16/253-353; B4N G93/233-301; B3MTR0/236-304; B3NZ90/246-314; Q9VEA9/242-310; B4QUH5/242-310; B4IB83/242-310; B4PL88/246-314; B4GLM4/255-323; Q293U2/255-323; B4JI50/203-271; B4K7H6/227-295; B4M0W2/211-279; Q7PYF1/252-320; B0X4C2/216-284; Q16ZH6/224-292; Q4RLU8/6-73; Q8R2S1/49-117; B4DSP6/49-117; Q5RA67/49-117; Q9Y6S9/49-117; Q32PG2/49-117; A9RII8/29-104; B8B1Z6/49-124; Q658G8/49-124; B4FVB5/49-124; Q944N4/90-165; A8MRR2/55-130; Q0WMJ4/55-130; O64630/55-130; B9RDF4/52-127; B9IC21/13-88; A7PY13/56-131; A5BB69/56-131; A5BIC4/76-120; A9V1R3/29-100; B3S0V7/15-93; C3XZ15/1-79; C3ZJS8/19-88; B7PXE3/98-174; B4NBP4/237-313; B4M0H8/223-299; B4K799/217-293; B4JII0/234-310; B4G437/239-315; B4QSF0/232-308; B3M3O1/235-311; B4HGG6/232-308; B3P8A3/232-308; Q298L4/239-315; B4PL32/232-308; Q8I0P1/232-308; Q16IA7/179-255; Q7QBW0/230-306; B0X289/2-60; Q4TCF6/6-91; Q4TCD9/16-91; Q6NW58/83-158; Q6AZT2/110-185; Q05AS3/113-188; Q9QYY8/117-193; Q9UBP0/119-195; A2VDN5/117-193; Q719N 1/116-192; Q5ZK92/116-192; B2RYN7/117-192; C3XW83/29-96; B7Q7T2/7-83; A7RQX2/15-88; Q4RRG4/9-85; C0H9Y4/20-96; Q0P3W0/20-96; Q4SG05/11-87; A8WFZ3/15-90; B3DLA2/21-97; Q8R1X6/19-95; Q3TVW1/19-95; A0JNJ3/19-95; Q4R7V2/19-95; Q8N0X7/19-95; B3KMI3/19-95; A8K6Q9/19-95; A2Q8K6/7-77; Q00204/6-77; B8MY71/5-77; Q9Y6Z8/5-77; Q0CUT6/6-77; A1CRW2/6-77; Q1DXZ5/5-72; B6QNP8/12-76; B0DXY2/11-78; Q7QGN5/7-67; B0WDD1/4-67; Q179Z1/4-67; Q179Z0/4-67; B7P5B6/89-157; Q5DBL1/86-142; A8P1B5/37-127; Q9R1S8/86-154; Q7Z479/86-154; B2RAM2/86-154; Q9Y6W3/86-154; A0FKG7/86-154; B0FG U2/86-154; Q499T5/86-154; C0H9M1/86-154; B4F6P1/86-154; Q4S467/86-149;Q6NVT4/42-110; C1BMZ4/11-74; A8PMC5/4-73; Q5D999/6-77; Q5D9R4/6-77; C4Q8N9/35-106; A7RL55/2-70; Q5I0J5/12-79; Q8VDV8/12-79; Q8WV92/12-79; B8ZZL5/12-79; A8YXZ4/12-79; Q6DJ62/7-75; C3XWE6/1-69; B0S8J9/9-77; B5XBB0/7-75; Q4S0N8/9-77; Q54KQ7/168-232; B3RXW5/5-72; A8PZJ1/282-350; C3Z907/423-490; Q4V7Q6/374-442; Q3U3Q1/375-444; B2RXB9/375-444; B4DFT0/386-455; B4DRQ7/375-444; B4DDG2/258-327; B4DFS6/285-354; B4DQN3/258-327; B2RXK3/375-444; A41G43/372-441; Q5ZJH6/375-444; Q7QEQ2/417-485; B0XAE0/287-363; B3M073/404-479; B4HKF5/399-474; B3P1R4/399-474; B4PUL9/399-474; B4QX75/399-474; B4JYT0/404-479; Q86P98/399-474; Q9VHF6/399-474; Q8T0L6/399-464; Q29BD1/399-474; B4NAJ4/403-478; B4LW06/400-475; B4K4Y3/397-472. Further MIT domains include those disclosed in Ciccarelli et al. (2003; Genomics 81: 437-41) or Patel et al. (2002; Nature Genetics 31: 347-8) or in the pdb (protein data bank) files (or related publications): 1wfd (Suetake et al.; Solution structure of mouse MIT domain); 1wr0 (Takasu et al. (2005). *Biochem Biophys Res Commun*, 334, 460-465.), 1yxr (Scott et al. (2005) Proc Natl Acad Sci USA. 102:13813-13818), 2cpt (Suetake et al.; Solution structure of MIT domain from human skd1), 2dI1 (Suetake et al.; Solution structure of MIT domain from human spartin), 2jq9 and 2jqh (Stuchell-Brereton et al. (2007). *Nature*, 449, 740-744.), 2k3w (C. Kieffer et al. (2008). *Dev Cell*, 15, 62-73.), 2v6x, 2v6y (T. Obita et al. (2007). *Nature*, 449, 735-739.), 2w2u (Samson et al. (2008). *Science*, 322, 1710-1713.), 2zam, 2zan, 2zao (all Inoue et al. (2008). *Traffic*, 9, 2180-2189.) or 3eab (Yang et al. (2008). *Nat Struct Biol*, 15, 1278-1286.).

In the chitin synthases identified herein, the MIT domain is located in an amino acid stretch from position 103 to 171 in SEQ ID NO: 4 (CHS1), corresponding to SEQ ID NO: 19, and from position 141 to 209 in SEQ ID NO: 2 (CHS2), corresponding to SEQ ID NO: 20.

Further example MIT domains show at least 80%, at least 85%, at least 90%, at least 95%, at least 98%, at least 99% or even 100% sequence identity to the MIT domains present in CHS1 (SEQ ID NO: 4), corresponding to SEQ ID NO: 20, and CHS2 (SEQ ID NO: 2), corresponding to SEQ ID NO: 19, or any one of the MIT domains present in the UniProt sequences or in the references listed above. All MIT domains disclosed herein have the biological function of the MIT domains present in CHS1 (SEQ ID NO: 4) and CHS2 (SEQ ID NO: 2). Said biological function can e. g. be evaluated by checking the location of a fusion protein comprising said MIT domain in a plant cell as outlined in the examples.

As used herein, the term "% sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S., Chapman & Hall. London, 1995), the homology alignment algorithm of Needleman and Wunsch (1970), the search for similarity method of Pearson and Lipman (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

An MIT domain may e. g. be operably linked with any of the following chitin synthases (Chitin UDP- acetyl-glucosaminyl transferases) which can be found in the different databases including amino acid sequences with the following identifiers (accession numbers): CHS1_AJECA (P30576) Chitin synthase 1 (EC 2.4.1.16) (Chitin-UDP acetyl-glucosaminyl transferase 1) (Class-I chitin synthase 1) from *Ajellomyces capsulata* (*Histoplasma capsulatum*); CHS1_AJEDE (P30579) Chitin synthase 1 (EC 2.4.1.16) (Chitin-UDP acetyl-glucosaminyl transferase 1) (Class-I chitin synthase 1) from *Ajellomyces dermatitidis* (Blastomyces dermatitidis); CHS1_ASPNG (P30581) Chitin synthase 1 (EC 2.4.1.16) (Chitin-UDP acetyl-glucosaminyl transferase 1) (Class-I chitin synthase 1) from *Aspergillus niger*; CHS1_BOTCI (P49603) Chitin synthase 1 (EC 2.4.1.16) (Chitin-UDP acetyl-glucosaminyl transferase 1) (Class-I chitin synthase 1) from *Botrytis cinerea* (Noble rot fungus) (*Botryotinia fuckeliana*); CHS1_CANAL (P23316) Chitin synthase 1 (EC 2.4.1.16) (Chitin-UDP acetyl-glucosaminyl transferase 1). from *Candida albicans* (Yeast); CHS1_CRYNV (O13356) Chitin synthase 1 (EC 2.4.1.16) (Chitin-UDP acetyl-glucosaminyl transferase 1) (Class-IV chitin synthase 1). {GENE: Name=CHS1}-*Cryptococcus neoformans* var. *grubii* (*Filobasidiella neoformans* var.*grubii*); CHS1_EMENI (P30583) Chitin synthase 1 (EC2.4.1.16) (Chitin-UDP acetyl-glucosaminyl transferase 1) (Class-I chitin synthase 1) (Fragment). {GENE: Name=chs1}—*Emericella nidulans* (*Aspergillus nidulans*); CHS1_EXODE (P30600) Chitin synthase 1 (EC2.4.1.16) (Chitin-UDP acetyl-glucosaminyl transferase 1) (Class-II chitin synthase 1). {GENE: Name=CHS1}—*Exophiala dermatitidis* (*Wangiella dermatitidis*); CHS1_EXOJE (P30585) Chitin synthase 1 (EC2.4.1.16) (Chitin-UDP acetyl-glucosaminyl transferase 1) (Class-I chitin synthase 1) (Fragment). {GENE: Name=CHS1}—*Exophiala jeanselmei*; CHS1_NEUCR (P29070) Chitin synthase 1 (EC2.4.1.16) (Chitin-UDP acetyl-glucosaminyl transferase 1) (Class-III chitin synthase 3). {GENE: Name=chs-1; ORFNames=B11H24.170, NCUO3611.1}—*Neurospora crassa*; CHS1_PHAEX (P30590); Chitin synthase 1 (EC2.4.1.16) (Chitin-UDP acetyl-glucosaminyl transferase 1) (Fragment). {GENE: Name=CHS1}—*Phaeococcomyces exophialae*; CHS1_PHYBL (P87073) Chitin synthase 1 (EC2.4.1.16) (Chitin-UDP acetyl-glucosaminyl transferase 1) (Class-II chitin synthase 1). {GENE: Name=chs1 }—*Phycomyces blakesleeanus*; CHS1_RHIAT (P30592) Chitin synthase 1 (EC2.4.1.16) (Chitin-UDP acetyl-glucosaminyl transferase 1) (Class-I chitin synthase 1) (Fragment). {GENE: Name=CHS1}—*Rhinocladiella atrovirens*; CHS1_RHIOL (P30594) Chitin synthase 1 (EC2.4.1.16) (Chitin-UDP acetyl-glucosaminyl transferase 1). {GENE: Name=CHS1}—*Rhizopus oligosporus*; CHS1_RHIRA (Q12632) Chitin synthase 1 (EC2.4.1.16) (Chitin-UDP acetyl-glucosaminyl transferase 1) (Class-II chitin synthase 1). {GENE: Name=CHS1}—*Rhizomucor racemosus*(*Mucor circinelloides f. lusitanicus*); CHS1_SCHCO (P30596); Chitin synthase 1 (EC2.4.1.16) (Chitin-UDP acetyl-glucosaminyl transferase 1) (Fragment). {GENE: Name=CHS1}—*Schizophyllum commune* (Bracket fungus); CHS1_SCHCO (P30597) Chitin synthase 1 (EC 2.4.1.16) (Chitin-UDP acetyl-glucosaminyl transferase 1). {GENE: Name=chs1; ORFNames=SPAC13G6.12c, SPAC24B11.01c}—*Schizosaccharomyces pombe* (Fission yeast); CHS1_TUBUN (P55003) Chitin synthase 1 (EC2.4.1.16) (Chitin-UDP acetyl-glucosaminyl transferase 1) (Fragment). {GENE: Name=CHS1}—*Tuber uncinatum* (Burgundy truffle); CHS1_USTMA (P30598) Chitin synthase 1 (EC2.4.1.16) (Chitin-UDP acetyl-glucosaminyl transferase 1) (Fragment). {GENE: Name=CHS1}—*Ustilago maydis* (Smut fungus); CHS1_XYLBA (P30603) Chitin synthase 1 (EC2.4.1.16) (Chitin-UDP acetyl-glucosaminyl transferase 1) (Fragment). {GENE: Name=CHS1}—*Xylohypha bantiana*; CHS1_YEAST (P08004) Chitin synthase 1 (EC2.4.1.16) (Chitin-UDP acetyl-glucosaminyl transferase 1). {GENE: Name=CHS 1; *Saccharomyces cerevisiae* (Baker's yeast); CHS2_AJECA (P30577) Chitin synthase 2 (EC2.4.1.16) (Chitin-UDP acetyl-glucosaminyl transferase 2) (Class-III chitin synthase 2) *Ajellomyces capsulata* (*Histoplasma capsulatum*); CHS2_AJEDE (P30580) Chitin synthase 2 (EC2.4.1.16) (Chitin-UDP acetyl-glucosaminyl transferase 2) (Class-II chitin synthase 2) {GENE: Name=CHS2}—*Ajellomyces dermatitidis* (*Blastomyces dermatitidis*) CHS2_ASPNG (P30582); Chitin synthase 2 (EC2.4.1.16) (Chitin-UDP acetyl-glucosaminyl transferase 2) (Class-II chitin synthase 2) (Fragment). {GENE: Name=chs2}—*Aspergillus niger*; CHS2_CANAL (P30572) Chitin synthase 2 (EC2.4.1.16) (Chitin-UDP acetyl-glucosaminyl transferase 2). {GENE: Name=CHS2}—*Candida albicans* (Yeast); CHS2_EXODE (P30601) Chitin synthase 2 (EC2.4.1.16) (Chitin-UDP acetyl-glucosaminyl transferase 2) (Class-I chitin synthase 2). {GENE: Name=CHS2}—*Exophiala dermatitidis* (*Wangiella dermatitidis*); CHS2_EXOJE (P30586) Chitin synthase 2 (EC2.4.1.16) (Chitin-UDP acetyl-glucosaminyl transferase 2) (Fragment). {GENE: Name=CHS2}—*Exophiala jeanselmei*; CHS2_NEUCR (P30589); Chitin synthase 2 (EC2.4.1.16) (Chitin-UDP acetyl-glucosaminyl transferase 2). {GENE: Name=chs-2; ORFNames=NCU05239.1}—*Neurospora crassa*; CHS2_PARBR (Q92444) Chitin synthase 2 (EC2.4.1.16) (Chitin-UDP acetyl-glucosaminyl transferase 2) (Class-II chitin synthase 2). {GENE: Name=CHS2}— *Paracoccidioides brasiliensis*; CHS2_PHAEX (P30591); Chitin synthase 2 (EC2.4.1.16) (Chitin-UDP acetyl-glucosaminyl transferase 2) (Class-II chitin synthase 2) (Fragment). {GENE: Name=CHS2}—*Phaeococcomyces exophialae*; CHS2_RHIAT (P30593) Chitin synthase 2 (EC2.4.1.16) (Chitin-UDP acetyl-glucosaminyl transferase 2) (Class-III chitin synthase 2) (Fragment). {GENE: Name=CHS2}—*Rhinocladiella atrovirens*; CHS2_RHIOL (P30595) Chitin synthase 2 (EC 2.4.1.16) (Chitin-UDP acetyl-glucosaminyl transferase 2). {GENE: Name=CHS2}—*Rhizopus oligosporus*; CHS2_SCHCO (074756) Chitin synthase-like protein 2. {GENE: Name=chs2; ORFNames=SPBC1709.01, SPBC1734.17}— *Schizosaccharomyces pombe* (Fission yeast); CHS2_USTMA (P30599) Chitin synthase 2 (EC2.4.1.16) (Chitin-UDP acetyl-glucosaminyl transferase 2) (Fragment). {GENE: Name=CHS2}—*Ustilago maydis* (Smut fungus); CHS2_XYLBA (P30604) Chitin synthase 2 (EC2.4.1.16) (Chitin-UDP acetyl-glucosaminyl transferase 2) (Class-II chitin synthase 2) (Fragment). {GENE: Name=CHS2}—*Xylohypha bantiana*; CHS2_YEAST (P14180); Chitin synthase 2 (EC2.4.1.16) (Chitin-UDP acetyl-glucosaminyl transferase 2). {GENE: Name=CHS 2; OrderedLocusNames=YBR038W; ORFNames=YBR0407}—*Saccharomyces cerevisiae* (Baker's yeast); CHS3_AJECA (P30578) Chitin synthase 3 (EC2.4.1.16) (Chitin-UDP acetyl-glucosaminyl transferase 3) (Class-II chitin synthase 3) (Fragment). {GENE:

Name=CHS3}—*Ajellomyces capsulata* (*Histoplasma capsulatum*); CHS3_CANAL (P30573) Chitin synthase 3 (EC2.4.1.16) (Chitin-UDP acetyl-glucosaminyl transferase 3) (Class-IV chitin synthase 3). {GENE: Name=CHS3}—*Candida albicans* (Yeast); CHS3_EXODE (P30602) Chitin synthase 3 (EC2.4.1.16) (Chitin-UDP acetyl-glucosaminyl transferase 3) (Class-III chitin synthase 3). {GENE: Name=CHS3}—*Exophiala dermatitidis* (*Wangiella dermatitidis*); CHS3_EXOJE (P30587); Chitin synthase 3 (EC2.4.1.16) (Chitin-UDP acetyl-glucosaminyl transferase 3) (Class-III chitin synthase 3) (Fragment). {GENE: Name=CHS3}—*Exophiala jeanselmei*; CHS3_NEUCR (P30588) Chitin synthase 3 (EC 2.4.1.16) (Chitin-UDP acetyl-glucosaminyl transferase 3). {GENE: Name=chs-3; ORFNames=G65A3.040}—*Neurospora crassa*; CHS3_YEAST (P29465) Chitin synthase 3 (EC 2.4.1.16) (Chitin-UDP acetyl-glucosaminyl transferase 3) (Class-IV chitin synthase 3). {GENE:. Name=CHS3; Synonyms=CAL1, CSD2, DIT101, KIT2; Ordered Locus Names=YBRO23C; ORFNames=YBRO305}—*Saccharomyces cerevisiae* (Baker's yeast); CHS4_MAGGR (O13353); Chitin synthase 4 (EC2.4.1.16) (Chitin-UDP acetyl-glucosaminyl transferase 4) (Class-IV chitin synthase 4). {GENE: Name=CHS4}—*Magnaporthe grisea* (Rice blast fungus) (*Pyricularia grisea*); CHS4_NEUCR (Q01285) Chitin synthase 4 (EC2.4.1.16) (Chitin-UDP acetyl-glucosaminyl transferase 4) (Class-IV chitin synthase 4). {GENE: Name=chs-4; ORFNames=NCU09324.1}—*Neurospora crassa*; CHS5_USTMA (013394) Chitin synthase 5(EC2.4.1.16) (Chitin-UDP acetyl-glucosaminyl transferase 5) (Class-IV chitin synthase 5). {GENE: Name=CHS5}—*Ustilago maydis* (Smut fungus); CHS6_USTMA (013395) Chitin synthase 6 (EC 2.4.1.16) (Chitin-UDP acetyl-glucosaminyl transferase 6) (Class-V chitin synthase 6). {GENE: Name=CHS6}—*Ustilago maydis* (Smut fungus); CHSA_AMPQU (Q12564); Chitin synthase A (EC 2.4.1.16) (Chitin-UDP acetyl-glucosaminyl transferase A) (Class-I chitin synthase A). {GENE: Name=CHSA}—*Ampelomyces quisqualis*; CHSA_EMENI (P30584) Chitin synthase A (EC 2.4.1.16) (Chitin-UDP acetyl-glucosaminyl transferase A) (Class-II chitin synthase A). {GENE: Name=chsA; Synonyms=chs2}—*Emericella nidulans*(*Aspergillus nidulans*); CHSB_EMENI (Q00757) Chitin synthase B (EC 2.4.1.16) (Chitin-UDP acetyl-glucosaminyl transferase B) (Class-III chitin synthase B). {GENE: Name=chsB}—*Emericella nidulans* (*Aspergillus nidulans*); CHSC_ASPFU (Q92197) Chitin synthase C (EC 2.4.1.16) (Chitin-UDP acetyl-glucosaminyl transferase C) (Class-III chitin synthase C). {GENE: Name=chsC}—*Aspergillus fumigatus* (Sartorya fumigata); CHSD_ASPFU (P78746) Chitin synthase D (EC 2.4.1.16) (Chitin-UDP acetyl-glucosaminyl transferase D) (Class-VI chitin synthase D). {GENE: Name=chsD}—*Aspergillus fumigatus* (Sartorya fumigata); CHSD_EMENI (P78611) Chitin synthase D (EC 2.4.1.16) (Chitin-UDP acetyl-glucosaminyl transferase D) (Class-V chitin synthase D). {GENE: Name=chsD; Synonyms=chsE}—*Emericella nidulans* (*Aspergillus nidulans*); CHSG_ASPFU (P54267); Chitin synthase G (EC 2.4.1.16) (Chitin-UDP acetyl-glucosaminyl transferase G) (Class-III chitin synthase G). {GENE: Name=chsG}—*Aspergillus fumigatus* (Sartorya fumigata); CHSX_USTMA (Q99126) Chitin synthase 1 (EC 2.4.1.16) (Chitin-UDP acetyl-glucosaminyl transferase 1). {GENE: Name=CHS1}—*Ustilago maydis* (Smut fungus); or CHSY_USTMA (Q99127) Chitin synthase 2 (EC 2.4.1.16) (Chitin-UDP acetyl-glucosaminyl transferase 2). {GENE: Name=CHS2}—*Ustilago maydis* (Smut fungus).

Operably linking can result in the MIT domain being present at the N-terminus, at the C-terminus or within a chitin synthase sequence as long as this position does essentially not impair the chitin synthase activity of the resulting protein. "Essentially not impair" in this regard means that the chitin synthase is still sufficiently active to provide for a detectable amount of positively charged polysaccharides in a plant cell wall, when expressed in said plant cell. This means that the chitin synthase has at least 20%, at least 30%, at least 40%, at least 50%, at least 60%, at least 70%, at least 80%, at least 90% or at least 100% of the chitin synthase activity of either CHS1 or CHS2. Methods of determining chitin synthase activity are known in the art and also disclosed in the present application.

In a particular embodiment the invention also provides variant sequences of SmCHS1 and SmCHS2 which may be obtained by induced generation of variation in vitro or in vivo. Several methods for in vitro induced generation of variant nucleotide sequences are available in the art including but not limited to DNA shuffling or directed evolution techniques as described in U.S. Pat. Nos. 5,605,793, 5,811,238 and 5,830,721. Methods for in vivo induced generation of variant nucleotide sequence are also well known in the art and may include exposure of *Saprolegnia monoica* to mutagens such as ionizing radiation, EMS, MMS or the like, followed by isolation of the chitin synthase 1 or 2 encoding nucleic acids, e.g. as elsewhere described herein. In another particular embodiment the SmCHS1 and SmCHS2, in particular the nucleic acids encoding them, can be modified by adapting the codon usage for the specific expression in plants. Such methods for codon-modification (or codon-adaptation which is an equivalent wording) for the expression in specific plants are well known in the art. SEQ ID NO: 18 depicts a variant SmCHS2 nucleotide sequence which is a codon-modified variant optimized for expression in cotton. SEQ ID NO: 18 encodes for the chitin synthase polypeptide depicted in SEQ ID NO: 2.

In another embodiment the invention provides a chimeric gene comprising the following operably linked DNA regions: 1) a plant-expressible promoter, 2) a DNA region coding for a chitin synthase polypeptide wherein the nucleotide sequence of the DNA region is at least 97% identical to SEQ ID NO: 1, or wherein nucleotide sequence of the DNA region is at least 90% identical to SEQ ID NO: 3, or wherein the nucleotide sequence of the DNA region comprises a nucleotide sequence which encodes a chitin synthase polypeptide which is at least 80% identical to SEQ ID NO: 2 or wherein the nucleotide sequence of the DNA region comprises a nucleotide sequence which encodes a chitin synthase polypeptide which is at least 90% identical to SEQ ID NO: 4 and 3) a transcription termination and polyadenylation region.

The chimeric genes according to the invention comprise a plant-expressible promoter. As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters and the like.

A plant-expressible promoter that controls initiation and maintenance of transcription preferentially in fiber cells is a promoter that drives transcription of the operably linked DNA region to a higher level in fiber cells and the underlying epidermis cells than in other cells or tissues of the plant. A higher level can be for example a transcription of at least 2-fold, at least 5-fold, at least 10-fold, at least 20-fold, at least 50-fold, at least 100-fold or at least 500-fold more in fiber cells and optionally the underlying epidermis cells than in other cells or tissues of the plant. Such definition also applies to the term "fiber selective promoter". In other words, the term includes a promoter that drives at least 2-fold, at least 5-fold, or at least 10-fold more transcription in fiber cells and optionally the underlying epidermis cells than in other cells or tissues of the plant. Such promoters include the promoter from cotton from a fiber-specific β-tubulin gene (as described in WO0210377), the promoter from cotton from a fiber-specific actin gene (as described in WO0210413), the promoter from a fiber specific lipid transfer protein gene from cotton (as described in U.S. Pat. No. 5,792,933), a promoter from an expansin gene from cotton (WO9830698) or a promoter from a chitinase gene in cotton (US2003106097) or the promoters of the fiber specific genes described in U.S. Pat. Nos. 6,259,003 or 6,166,294 or the promoters derived from the E6 family as disclosed in U.S. Pat. No. 6,096,950. In a particular embodiment the plant-expressible promoter is a constitutive promoter. As discussed in example 3, last 6 lines, expressing the chitin synthase of the invention does not cause differences in plant growth as compared to untransformed plants.

In a particular embodiment the invention provides a plant cell comprising a chimeric gene herein described before.

The chimeric gene may be introduced into a plant cell by methods well-known in the art. "Introducing" in connection with the present application relate to the placing of genetic information in a plant cell or plant by artificial means. This can be effected by any method known in the art for introducing RNA or DNA into plant cells, tissues, protoplasts or whole plants.

A number of methods are available to transfer DNA into plant cells or plants. *Agrobacterium*-mediated transformation of cotton has been described e.g. in U.S. Pat. No. 5,004,863, in U.S. Pat. No. 6,483,013 or in WO2000/71733.

Plants or plant cells may also be transformed by particle bombardment: Particles of gold or tungsten are coated with DNA and then shot into young plant cells or plant embryos. This method also allows transformation of plant plastids. Cotton transformation by particle bombardment is reported e.g. in WO 92/15675.

Viral transformation (transduction) may be used for transient or stable expression of a gene, depending on the nature of the virus genome. The desired genetic material is packaged into a suitable plant virus and the modified virus is allowed to infect the plant or plant cell. The progeny of the infected plants is virus free and also free of the inserted gene. In an exemplary viral transformation protocol, DNA such as DNA comprising the chimeric gene described herein as well as a helper virus, can be introduced into whole plants by mechanical inoculation with DNA comprising the chimeric gene described herein alone or with virions containing the said DNA. The selection of the best suited transformation protocol including the manner and parameters of transformation, timing of transformation, etc. is well within the knowledge of persons of ordinary skill in the art. Suitable methods are described or further detailed e. g. in WO 90/12107, WO 03/052108 or WO 2005/098004.

In another particular embodiment the invention provides a plant consisting essentially of plant cells comprising a chimeric gene herein described before. In a particular embodiment the plant is a transgenic cotton plant.

Apart from the methods for introducing the chimeric gene described above, said chimeric gene may also be introgressed into a plant. "Introgressing" means the integration of a gene in a plant's genome by natural means, i. e. by crossing a plant comprising the chimeric gene described herein with a plant not comprising said chimeric gene. The offspring can be selected for those comprising the chimeric gene.

The plant may be any fiber producing plant such as cotton. Other examples include other fiber producing plants such as hemp, jute, flax and woody plants, including but not limited to *Pinus* spp., *Populus* spp., *Picea* spp., *Eucalyptus* spp. etc.

In another particular embodiment the invention provides a transgenic seed comprising a chimeric gene as herein described before.

In yet another embodiment the invention provides a method for the manufacture of a plant cell wall comprising positively charged polysaccharides, said method comprises 1) expressing a chimeric gene as outlined herein before in a plant or plant cell and 2) isolating said plant cell wall. Said isolating is from the plant obtained after carrying out step 1).

In a specific embodiment said method for manufacturing (or production which is an equivalent wording) produces positively charged polysaccharides in a plant secondary cell wall. In another particular embodiment said method for manufacturing produces chitin in a plant secondary cell wall. In another particular embodiment said method for manufacturing produces chitosan in a plant secondary cell wall, for example due to the presence and expression of a further chimeric gene comprising a chitin deacetylase as described further below. In a particular embodiment said plant cell wall, or said plant secondary cell wall is a cotton plant cell wall or a cotton secondary plant cell wall. In a particular embodiment said cotton plant cell wall, or said cotton secondary cell wall is present in a cotton fiber.

The invention further provides plant cell walls including the cell walls obtained from plant cells using the methods according to the invention, and fibers comprising said cell walls.

Such plant cell walls comprise positively charged polysaccharides, such as N-acetylglucosamine polymers or chitin, embedded into the cellulose. These plant cell walls may be further modified, e.g. partly or completely deacetylated such that oligomers comprising glucosamine residues are obtained. The amino-group of the resulting glucosamines is chemically more reactive than the aminoacetyl group of N-acetylglucosamine or the hydroxyl group of cellulose. In a particular embodiment plant cell walls, in particular plant secondary cell walls, comprising chitin can be further modified by means of a chemical deacetylation step. In another particular embodiment the method for manufacturing positively charged polysaccharides in a plant cell wall can be carried out by expressing two chimeric genes in a plant or plant cell, one chimeric gene being a chitin synthase of the invention together with a chimeric chitin deacetylase. A chitin deacetylase in enzymology, is an enzyme (EC 3.5.1.41) that catalyzes the chemical reaction:

chitin + H$_2$O ⇌ chitosan + acetate

Thus, the two substrates of this enzyme are chitin and H$_2$O, whereas its two products are chitosan and acetate. This enzyme belongs to the family of hydrolases, those acting on carbon-nitrogen bonds other than peptide bonds, specifically in linear amides. The systematic name of this enzyme class is chitin amidohydrolase.

In a particular embodiment the plant cell wall obtained according to the invention, particularly those which have been subjected to a deacetylation step, for example in vivo as described above or after harvest of the cell wall, can be further chemically modified. Products containing such plant cell walls, such as fibers, yarns or fabrics have qualities resembling those of the cellulose-chitosan blends described in the art, including improved dyeability, improved inhibition of e.g. dermatophytes, controlled drug release etc.

In a specific embodiment, the invention provides cotton fibers obtained from or which can be obtained from cotton plants according to the methods of the invention. In other words, cotton fibers are provided from cotton plants comprising in the genome, such as the nuclear genome, of their cells a chimeric gene comprising a plant-expressible promoter operably linked to a DNA region coding for a chitin synthase 1 or 2 according to the invention or a combination of two chimeric genes coding for the chitin synthase genes 1 and 2 according to the invention. Particular embodiments of DNA coding regions or promoters comprised in the chimeric genes transferred into cotton plants are as described elsewhere in this document.

The cotton fibers according to the invention can be distinguished from naturally occurring cotton fibers, i.e. cotton fibers obtained from an isogenic line which does not comprise a chimeric gene according to the invention, by the capacity of such fibers for increased staining with anionic dyes (including e.g. Congo Red), by the capacity of such fibers for increased staining with amine-reactive dyes (including e.g. tetrafluorophenyl ester). The cotton fibers according to the invention also have the capacity of binding of Wheat germ agglutinin which binds chitin. The cotton fibers according to the invention can also be distinguished from naturally occurring cotton fibers by direct detection of the N-acetyiglucosamine and GlcNAc polymers, optionally after treatment of the fiber cell wall material with chitinase. The cotton fibers according to the invention may also be distinguished by their increased nitrogen content.

Cotton fibers according to the invention can also be distinguished from the chitosan coated fibers of the prior art, in that the positively charged polymers are evenly distributed in the secondary plant cell walls making up the fibers as opposed to the surface coated chitosan fibers of the prior art. Accordingly, in microscopical sections of cotton fibers, stained e.g. with WGA or with congo red or with tetrafluorophenyl as described hereinafter, the dyes will be distributed evenly throughout the cell walls making up the cotton fibers, whereas in chitosan-coated fibers, the staining will be concentrated at the coat of chitosan located as a sheet at the surface of the treated fibers.

The increased staining of the plant cell wall material according to the invention, by anionic dyes such as congored can be quantified e.g. by dying a uniform amount of material under standard conditions, spreading out the material over a standardized area (such as a well in a multiwell plate) digitalizing a picture of the area for the gray scale of the colored layer of material. The less gray, the more stained the plant cell wall material is. In this way, cotton fibers and cell wall material according to the invention showed an increase of at least about 5% in staining by congo-red compared to control cell wall material or fibers from isogenic plant lines without a chitin synthase encoding gene. In a particular embodiment the plant cell material obtained according to the invention can be stained with commercial dyes including cotton reactive dyes (e.g. Reactive Red 120, Levafix Blue CA), acid dyes (Acid Orange 7, Acid Blue 281) and wool reactive dyes (e.g. Reactive Red 116, Realan Amber EHF). In an example, the cotton fibers and the cell wall material according to the invention show an increase of at least about 5%, at least about 10%, at least 20%, at least 30%, at least 40%, at least 50% at least 60, at least 70%, at least 80%, at least 90% or even at least 100% such as 2-fold, 5-fold or 10-fold in staining as compared to said fibers and material not comprising a chitin synthase encoding gene.

The capacity of the novel cotton fibers to specifically bind wheat germ agglutin (detectable by the coupled fluorophoric group) is a clear distinguishing feature of the provided novel cotton fibers over the naturally occurring cotton fibers. Except for a very low background fluorescence, naturally occurring cotton fibers do not stain/fluoresce when treated with WGA—alexa fluor 488 or 555. The fluorescence of cotton fibers increases at least 5 times when chitin polymers are present. Accordingly, the invention provides cotton fibers which are capable of specifically binding wheat germ agglutinin, or WGA coupled to a flurophore, such as WGA Alexa 488 or WGA Alexa 555 or which, when treated with WGA Alexa 488 or WGA Alexa 555 provide a bright fluorescence under UV light. This fluorescence is not restricted to the surface of the cotton fiber but is distributed throughout the cell wall of the fiber cells.

Cotton fibers according to the invention can also be distinguished from only chitosan coated fibers by applying the detection method disclosed in WO2010/015423 and checking for the presence of the chimeric gene of the invention in the fibers.

Wherever the methods of the invention are directed to introduction of a chimeric gene in a plant cell, it will be clear that such methods can also be applied in cases whereby the plant cell is incorporated into a mature plant. E.g. transgenic cells may be regenerated into transgenic plants according to established methods.

Methods to transform plants cells and plants are well known in the art. Methods to transform cotton plants are also well known in the art. Agrobacterium-mediated transformation of cotton has been described e.g. in U.S. Pat. No. 5,004,863 or in U.S. Pat. No. 6,483,013 and cotton transformation by particle bombardment is reported e.g. in WO 92/15675.

The chimeric genes may be introduced by transformation in cotton plants from which embryogenic callus can be derived, such as Coker 312, Coker310, Coker 5Acala SJ-5, GSC25110, FiberMax 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA, Fibermax® FM5013, FM5015, FM5017, FM989, FM832, FM966 and FM958, FM989, FM958, FM832, FM991, FM819, FM800, FM960, FM966, FM981, FM5035, FM5044, FM5045, FM5013, FM5015, FM5017 or FM5024 and plants with genotypes derived thereof.

"Cotton" as used herein includes *Gossypium hirsutum, Gossypium barbadense, Gossypium arboreum* and *Gossypium herbaceum* or progeny from crosses of such species with other species or crosses between such species.

The methods and means of the current invention may also be employed for other plant species such as hemp, jute, flax and woody plants, including but not limited to *Pinus* spp., *Populus* spp., *Picea* spp., *Eucalyptus* spp. etc.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

The chimeric gene of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides, and others which confer tolerance to certain insects or those which confer tolerance to certain diseases.

Such genes are in described for example in published PCT Patent Applications WO 91/02071 and WO95/06128.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435, 6,566,587 and WO 97/04103), a gene encoding glyphosate oxydoreductase (U.S. Pat. No. 5,463,175), or a gene encoding the HPPD enzyme for tolerance to HPPD inhibitor herbicides such as isoxazoles (WO 96/38567).

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The following non-limiting Examples describe the methods for altering plant cell walls. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

The transformed plant cells and plants obtained by the methods described herein may be further used in breeding procedures well known in the art, such as crossing, selfing, and backcrossing. Breeding programs may involve crossing to generate an F1 (first filial) generation, followed by several generations of selfing (generating F2, F3, etc.). The breeding program may also involve backcrossing (BC) steps, whereby the offspring is backcrossed to one of the parental lines, termed the recurrent parent.

The transgenic plant cells and plants obtained by the methods disclosed herein may also be further used in subsequent transformation procedures, e. g. to introduce a further chimeric gene.

The plants comprising the chimeric gene disclosed herein may further be treated with cotton herbicides such as Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; cotton insecticides such as Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; and cotton fungicides such as Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin.

Throughout the description and Examples, reference is made to the following sequences represented in the sequence listing:

SEQ ID No: 1: nucleotide sequence of the *Saprolegnia monoica* chitin synthase 2 gene SEQ ID No: 2: amino acid sequence of the *Saprolegnia monoica* chitin synthase 2 gene SEQ ID No: 3: nucleotide sequence of the *Saprolegnia monoica* chitin synthase 1 gene SEQ ID No: 4: amino acid sequence of the *Saprolegnia monoica* chitin synthase 1 gene SEQ ID NOs: 5-17 are synthetic primers for which the sequences are depicted in Table 1.

SEQ ID NO: 18: modified nucleotide sequence of *Saprolegnia monoica* chitin synthase 2 (codon optimized for expression in cotton)

SEQ ID No: 19: amino acid sequence of the MIT domain of *Saprolegnia monoica* chitin synthase 1

SEQ ID NO: 20: amino acid sequence of the MIT domain of *Saprolegnia monoica* chitin synthase 2

SEQ ID NO: 21: nucleotide sequence of a *Saprolegnia parasitica* chitin synthase gene SEQ ID NO: 22: amino acid sequence encoded by the *Saprolegnia parasitica* chitin synthase gene of SEQ ID NO: 21

SEQ ID NO: 23: nucleotide sequence of a *Saprolegnia parasitica* chitin synthase gene SEQ ID NO: 24: amino acid sequence encoded by the *Saprolegnia parasitica* chitin synthase gene of SEQ ID NO: 23

EXAMPLES

1. Cloning of Chitin Synthase Genes from *Saprolegnia monoica*

The oomycete *Saprolegnia monoica* Pringsheim 53-967 Dick was obtained from the "Centraal Bureau voor Schimmel Culturen" (CBS, Baarn, The Netherlands) and maintained on Potato Dextrose Agar in 90-mm Petri dishes. The mycelium used for the experiments was grown in the liquid medium of Machlis (Machlis L. (1953) Am. J. Bot. 40, 449-460) for 3-5 days at 25° C. in the dark.

Total RNA was extracted from 100 mg of 3-days old *S. monoica* mycelium, using the RNeasy Plant Mini Kit (Qiagen), coupled with the on-column DNaseI digestion. Reverse transcription was carried out with 4.5 μg total RNA using the Superscript III First Strand cDNA Synthesis kit (Invitrogen) following the manufacturer's instructions. 1 μl of the synthesized cDNA was used in the PCR reactions using the primers CHS2Fwd and CHS2Rev which were designed based on the sequence deposited under the accession number U19946 (this sequence is also disclosed in Mort-Bontemps M. et al (1997) *Microbiology* 143, 2009-2020 wherein a chitin synthase 2 (CHS2) sequence is depicted in FIG. 3 of said reference), for the amplification of the CHS2 sequence. The RNA ligase-mediated RACE kit (RLM-RACE, Ambion) was used to isolate and determine the sequence of the 3' end of CHS2. The 3' end of CHS2 was obtained with the primers CHS2Fwd1 and CHS2Fwd2. The complete full-length CHS2 coding sequence (depicted in SEQ ID NO: 1) was amplified from *S. monoica* mycelium cDNA using the primers CHS2Fwd and CHS2FLRev. This resulting sequence was cloned into pENTR-D-TOPO (Invitrogen) using the Gateway technology according to the manufacturer's instructions. The construct was transformed into One Shot TOP10 chemically competent cells (Invitrogen) and the nucleotide sequence was determined (MWG, Germany). It was observed that the disclosed coding sequence of the *S. monoica* CHS2 (accession number U19946) is only 96% identical to the isolated CHS2 sequence depicted in SEQ ID NO: 1. The differences in the nucleotide sequence are due to a number of small deletions in the coding sequence of the chitin synthase 2 disclosed with accession number U19946. As a consequence the translation of the coding sequence depicted in SEQ ID NO: 1 is only 79% identical to the translated coding sequence of accession number U19946. The latter is caused by small deletions in the nucleotide sequence of U19946, which leads to frame shifts with respect to the translation of SEQ ID NO: 1, upon translation of the coding sequence of U19946. It was apparent that SEQ ID NO: 2 comprises the conserved Microtuble Interacting and Trafficking molecule domain (MIT domain) which is absent in the chitin synthase protein translated from the accession U19946.

The sequences were edited using the software BioEdit (Hall TA (1999) BioEdit: a user-friendly biological sequence alignment editor and analysis—on the world wide web at mbio.ncsu.edu/BioEdit/bioedit.html). Alignment was performed using ClustalW (Larkin MA et al (2007) Bioinformatics 23, 2947-2948). SmCHS 1 and SmCHS2 full-length sequences were used to perform a BLASTp search against non redundant protein database from the National Centre for Biotechnology (NCBI, on the world wide web at ncbi.nlm.nih.gov).

Table 1 depicts the sequence of the primers:

| | |
|---|---|
| CHS2Fwd, SEQ ID NO: 5 | CACCATGAGTGACCAGCTCGAC CTCGCGGC |
| CHS2Rev, SEQ ID NO: 6 | TGCTCTCTGCACGGGCAACCAC AACCCGAC |
| CHS1Fwd, SEQ ID NO: 7 | AATGAGGACGAGAACGAGCTCC GGTCG |
| CHS1Rev, SEQ ID NO: 8 | AGCTTGTAAAAGGACGACTTGG TTGGC |
| CHS1Rev1, SEQ ID NO: 9 | TCTCCTTGGTCATTTGCAGCGA GTGTTC |
| CHS1Rev2, SEQ ID NO: 10 | CAGAACGTTGTTGCAAACCTTG CGGAGT |
| CHSFwd1, SEQ ID NO: 11 | TCCGGTCGACACTCCGCAAGGT TTGCAA |
| CHS1Fwd2, SEQ ID NO: 12 | ACTACACGGTCCTCCTCGATGT TGGGAC |
| CHS2Fwd1, SEQ ID NO: 13 | TGTCGGTGGCTTGATTGTCTTT GC |
| CHS2Fwd2, SEQ ID NO: 14 | TTTGGCTCTACGTTGTGACGGA CT |
| CHS1FLFwd, SEQ ID NO: 15 | CACCATGCCGCCCAAGCGACCG ACGACCGA |
| CHS1FLRev, SEQ ID NO: 16 | CTAGCGCATGCGGTTGTACGGC GCTTGG |
| CHS2FLRev, SEQ ID NO: 17 | TTAGACTTGTTGGTAGGCGCCG CCGCGG |

Two primers (CHS1Fwd and CHS1Rev) were designed based on the partial sequence of the *S. monoica* chitin synthase 1 (CHS1), corresponding to the accession number U42304, for the amplification of a conserved region of CHS1. The RNA ligase-mediated RACE kit (RLM-RACE, Ambion) was used to amplify the 5' and 3' ends of CHS1. The following sets of nested reverse primers were used to obtain the 5' end of CHS1: CHS1Rev1 and CHS1Rev2. The nested forward primers CHSFwd1 and CHS1Fwd2 were used to isolate the 3' end. Full-length CHS1 was amplified from *S. monoica* mycelium cDNA to confirm the complete sequence using the primers CHS1FLFwd and CHS1FLRev for the amplification of the coding sequence of the CHS1 gene. The full-length gene was cloned into pENTR-D-TOPO (Invitrogen) using the Gateway technology according to the manufacturer's instructions. The construct was transformed into One Shot TOP10 chemically competent cells (Invitrogen) and the nucleotide sequence was determined by sequencing (MWG, Germany). All PCR reactions were carried out using Phusion High-Fidelity DNA Polymerase (Finnzymes), according to the manufacturer's instructions. The coding region of the chitin synthase 1 nucleotide sequence is depicted in SEQ ID NO: 3. The amino acid sequence of the chitin synthase 1 is depicted in SEQ ID NO: 4.

2. Construction of Chimeric Plant-Expressible Genes Encoding a *Saprolegnia monoica* Chitin Synthase 2 (CHS2) Protein Using standard recombinant DNA techniques, a plant expressible *Saprolegnia monoica* CHS2 chimeric gene was constructed containing the following operably linked DNA fragments:

- a 35S promoter region from CaMV
- a DNA fragment coding for an untranslated leader sequence (5'Cab22L)
- a DNA fragment coding for CHS2 of *Saprolegnia monoica* (depicted in SEQ ID NO: 1)
- a transcription termination and polyadenylation signal from the octopine synthase gene Briefly, this construct was generated by PCR-cloning the CHS2 gene into the Gateway entry vector pENTR/D/TOPO, using the directional TOPO cloning kit (Invitrogen), according to the manufacturer's instructions. The PCR reaction was carried out using Phusion DNA polymerase (Finnzymes). The resulting entry vector was recombined into the destination vector pEarleyGate 103 using the Gateway LR Clonase Enzyme Mix (Invitrogen) (Earley K W et al (2006) *Plant J.* 45: 616-629). All constructs were sequence verified by sequence analysis. The selection marker for plant transformation was the bar gene providing resistance to phosphinotricin. The recombinant binary vector pEarleyGate 103 comprising the SmCHS2 gene was used to transform the *Agrobacterium* strain C58C1 (Voinnet O. et al (2003) *Plant J.* 33: 949-956) which was used to transform *Arabidopsis thaliana* by means of the floral dip method (Clough S J and Bent A F (1998) *Plant J.* 16: 735-743). The transformed *A. thaliana* plants comprising the chimeric *Saprolegnia monoica* chitin synthase 2 did not differ in growth compared to the untransformed *A. thaliana* plants. This is in contrast with the reduced growth of the transgenic *A. thaliana* plants comprising the *Neurospora crassa* chitin synthase operably linked with a Golgi localisation signal (as disclosed in WO2006/136351, see example 9).

3. Histochemical Analysis of the Trichomes of Recombinant *Arabidopsis thaliana*

Trichomes (plant hairs) in *Arabidopsis thaliana* are large non-secreting epidermal cells with a characteristic three-dimensional structure. Because trichomes are easily accessible to a combination of genetic, cell biological and molecular methods we used mature trichomes derived from recombinant *A. thaliana* plants produced in example 2 for the analysis of the plant cell walls of SmCHS2-transformed *A. thaliana* plants. During our recent investigations we observed that the cell wall analysis of hairy root cultures (see WO2006/136351, example 2) leads to similar results as the cell wall analysis of mature trichomes (the latter are also less cumbersome to establish and easier to isolate than hairy root cultures).

Trichomes were histochemically stained to visualize different compounds of the cells, and analyzed microscopically.

N-acetylglucosamine can be detected e. g. after immunological reaction with IgM monoclonal antibodies to N-acetylglucosamine (BIODESIGN). Chitin can be detected by for example using Wheat Germ Agglutin-Alexa Fluor 555 or alternatively by using a rhodamine-conjugated chitin-binding probe. The latter is a recombinant fusion protein that binds specifically to chitin. The fusion protein comprises a small (5 kDa) chitin-binding domain (CBD) derived from the C-terminal region of chitinase A1 of *Bacillus circulans* WL-12 fused to the C-terminus of maltose-binding protein (43 kDa) from *E. coli*. The fusion protein is labeled using tetramethylrhodamine isothiocyanate (TRITC) following standard methods. We purchased the rhodamine-conjugated chitin-binding probe from New England BioLabs (catalogue number P 5210).

The histochemically stained trichomes were examined by means of fluorescence microscopy, using an Axioplan 2 microscope (Zeiss, Jena, Germany) equipped with Apotome (Zeiss) to allow optical sections. Axio Vision 4.2 (Zeiss) was used for image processing.

Calcofluor staining of plant cell walls can be carried out with the following protocol. Calcofluor White (or Fluorescent Brightener 28) is a colourless organic compound that fluoresces in a clear bluish color under ultraviolet radiation ($\lambda$max=350 nm). The specimen (i.e. the trichome) to be stained is immersed for 15 to 30 minutes in culture medium or PBS (buffer solution) comprising Fluorescent Brightener 28 at 50 µg/mL final concentration. The specimen is then washed with medium or buffer, and samples are examined using a microscope equipped for fluorescence microscopy using Zeiss filter set 18. Cell walls fluoresce in a clear bluish color. Recombinant mature trichomes comprising the SmCHS2 chimeric gene are immunohistochemically stained for the presence of N-acetylglucosamine and subsequently stained with Calcofluor to visualize the cell walls. As can be observed from the superposition of the optical sections, the presence of N-acetylglucosamine is exclusively detected in the cell walls of recombinant trichomes.

Method for Wheat Germ Agglutinin-Alexa Fluor 555 Staining or Staining with the Rhodamine-Conjugated Chitin-Binding Probe:

Mature leaves comprising trichomes were isolated after about three weeks from in vitro generated transgenic *Arabidopsis* plants (i.e. recombinant plants comprising SmCHS2 according to example 2) and also from control *Arabidopsis* plants (i.e. non-transformed plants). The leaves were first fixed in a fixative (10% formalin, 0.25% glutaraldehyde in PBS) for 1 hour. The sample was vacuum infiltrated and the fixative was refreshed and incubated with the leaves for another 3 hours. Finally, after fixation the leaves could be further processed or stored at 4° C. for some days. In a next step fixated leaves were washed (for 60 minutes) with PBS followed by washing with PBT for 60 minutes (i.e. PBS+ 0.1% Tween20). The leaves were subsequently incubated with wheat germ agglutinin-Alexa Fluor 555 (Alexa fluor 555 TFP ester is available as a kit from the company Molecular Probes) in PBT (3 mg/ml) for 4 to 6 hours. Or alternatively the leaves were incubated with the rhodamine-chitin-binding-probe for 16 hours. After the incubation the fluorochrome or the rhodamine-chitin-binding-probe was washed away (twice with PBT and once with PBS).

The stained recombinant trichomes were examined at the edges of the leaves using fluorescence microscopy e.g. with Zeiss filter 38. It was observed that the cell wall material from recombinant trichomes reproducibly stained more intense than cell wall material from control plants (see FIG. 1).

4. Fiber Specific Expression of a Chitin Synthase in Cotton

Transgenic cotton plants comprising a chimeric chitin synthase 2 gene as outlined in example 2, under control of the F286 fiber-selective promoter (which is disclosed in US2003/106097) as well as transgenic plants comprising two chimeric genes, i. e. said chimeric chitin synthase 2 gene under control of the F286 promoter and a glutamine:fructose-6-phosphate amidotransferase (gfa) gene under control of said F286promoter, or said chimeric chitin synthase 2 gene under the control of the E6 promoter and a gfa gene under control of the E6 promoter, have been generated using the transformation method as described in U.S. Pat. No.6,483,013. Fibers from these transgenic cotton plants are isolated and used to produce yarns and fabrics with improved reactivity, such as improved dyeability. Fibers isolated from cotton bolls of transgenic plants have an increased amount of N-acetylglucosamine polymers which are evenly distributed throughout the cell wall.

5. Cotton Fibers with Increased Reactivity

Transgenic cotton plants comprising a chimeric SmCHS2 coding region operably linked to a fiber-specific promoter have been generated as described in Example 4. Mature cotton fibers are harvested from these plants and can be stained with Congo Red or can be reacted with WGA-Alexa fluor 555. In addition, the resulting mature cotton fibers can be stained with commercial dyes including cotton reactive dyes (e.g. Reactive Red 120, Levafix Blue CA), acid dyes (Acid Orange 7, Acid Blue 281) and wool reactive dyes (e.g. Reactive Red 116, Realan Amber EHF).

WGA-Alexa 555 Staining

Cotton fibers do not need to be dehydrated or permeabilized. Instead, lipids and waxes are removed by treating the fibers for 3 times 10 minutes in a chloroform:methanol mixture (1:1), follow by twice a treatment of 10 minutes in acetone and twice 5 minutes in ether. The fibers are allowed to air dry.

Fibers can be stained with WGA-Alexa555, WGA-Alexa488 or WGA-tetramethylrhodamine.

The fibers are placed in blocking solution (150 mM NaCL, 10 mM sodiumphosphate buffer pH 7.4; 0.1% Tween 20 and 1% bovine serum albumin) and are incubated for one hour. Thereafter, the buffer is replaced by the same buffer containing WGA-fluorochrome and incubated for 4 hrs. The WGA-fluorochrome solution is replaced by blocking solution, washed 10 minutes, followed by 3 times 10 min washing with blocking solution without BSA, and 2 times 5 min washing with blocking solution without BSA and without Tween. The stained fibers are mounted on a microscope slide and evaluated by means of fluorescence microscopy (Axioplan 2 (Zeiss, Jena, Germany) using Filterset 38 (exitation: BP470/40; emission: BP525/50) for Alexa fluor 488 conugate or Filterset (exitation: BP546/12; emission: BP575-640) for Alexa fluor 555 or tetramethylrhodamine conjugate. Whereas no specific fluorescence can be detected in cotton fibers from non-transgenic cotton plants, a bright fluorescence is detectable in cotton fibers from transgenic cotton plants comprising a chimeric SmCHS2 gene. Virtual microscopic sections of the cotton fibers show that the WGA-fluor555 is evenly distributed throughout the secondary cell wall of the cotton fiber cells.

The invention claimed is:

1. A plant cell comprising a chimeric gene comprising the following operably linked DNA regions:
   a. a plant-expressible promoter,
   b. a DNA region coding for a chitin synthase polypeptide, said DNA region comprising:
      i. a nucleotide sequence which encodes a chitin synthase polypeptide, wherein said polypeptide is at least 95% identical to SEQ ID NO: 2; or
      ii. a nucleotide sequence which encodes a chitin synthase polypeptide, wherein said polypeptide is at least 95% identical to SEQ ID NO: 4;
   c. a transcription termination and polyadenylation region.

2. A plant comprising the at least one plant cell of claim 1.

3. The plant of claim 2, wherein said plant is cotton.

4. Fibers comprising a chimeric gene comprising the following operably linked DNA regions:
   a. a plant-expressible promoter,
   b. a DNA region coding for a chitin synthase polypeptide, said DNA region comprising:
      i. a nucleotide sequence which encodes a chitin synthase polypeptide, wherein said polypeptide is at least 95% identical to SEQ ID NO: 2; or
      ii. a nucleotide sequence which encodes a chitin synthase polypeptide, wherein said polypeptide is at least 95% identical to SEQ ID NO: 4;
   c. a transcription termination and polyadenylation region obtainable from the plant according to claim 2.

5. A transgenic seed comprising a chimeric gene comprising the following operably linked DNA regions:
   a. a plant-expressible promoter,
   b. a DNA region coding for a chitin synthase polypeptide, said DNA region comprising:
      i. a nucleotide sequence which encodes a chitin synthase polypeptide, wherein said polypeptide is at least 95% identical to SEQ ID NO: 2; or
      ii. a nucleotide sequence which encodes a chitin synthase polypeptide, wherein said polypeptide is at least 95% identical to SEQ ID NO: 4;
   c. a transcription termination and polyadenylation region.

6. A method for the manufacture of a plant cell wall comprising positively charged polysaccharides, said method comprising
   a. expressing a chimeric gene comprising the following operably linked DNA regions:
      i. a plant-expressible promoter,
      ii. a DNA region coding for a chitin synthase polypeptide, said DNA region comprising:
         1. a nucleotide sequence which encodes a chitin synthase polypeptide, wherein said polypeptide is at least 95% identical to SEQ ID NO: 2; or
         2. a nucleotide sequence which encodes a chitin synthase polypeptide, wherein said polypeptide is at least 95% identical to SEQ ID NO: 4;
      iii. a transcription termination and polyadenylation region,
   b. and isolating said plant cell wall.

7. The method according to claim 6 wherein said plant cell wall is a cotton plant cell wall.

8. The method according to claim 7 wherein said cotton plant cell wall is present in a cotton fiber.

9. The plant cell, plant, fiber, or seed according to any one of claims 1-4 or 6, wherein said DNA region comprises:
   i. a nucleotide sequence which encodes a chitin synthase polypeptide, wherein said polypeptide is at least 98% identical to SEQ ID NO: 2; or
   ii. a nucleotide sequence which encodes a chitin synthase polypeptide, wherein said polypeptide is at least 98% identical to SEQ ID NO: 4.

10. The plant cell, plant, fiber, or seed according to any one of claims 1-4 or 6, wherein said DNA region comprises:
   i. a nucleotide sequence which encodes a chitin synthase polypeptide according to SEQ ID NO: 2; or
   ii. a nucleotide sequence which encodes a chitin synthase polypeptide, according to SEQ ID NO: 4.

11. The method according to claim 6, wherein said DNA region comprises:
   i. a nucleotide sequence which encodes a chitin synthase polypeptide, wherein said polypeptide is at least 98% identical to SEQ ID NO: 2; or
   ii. a nucleotide sequence which encodes a chitin synthase polypeptide, wherein said polypeptide is at least 98% identical to SEQ ID NO: 4.

12. The method according to claim 6, wherein said DNA region comprises:
   i. a nucleotide sequence which encodes a chitin synthase polypeptide according to SEQ ID NO: 2; or
   ii. a nucleotide sequence which encodes a chitin synthase polypeptide, according to SEQ ID NO: 4.

13. The plant cell, plant, fiber, or seed according to any one of claims 1-4 or 6, wherein said promoter is a constitutive promoter.

14. The plant cell, plant, fiber, or seed according to any one of claims 1-4 or 6, wherein said promoter is a fiber-selective promoter.

15. The method according to claim 6, wherein said promoter is a constitutive promoter.

16. The method according to claim 6, wherein said promoter is a fiber-selective promoter.

* * * * *